(12) United States Patent
Hoffer et al.

(10) Patent No.: US 12,318,595 B2
(45) Date of Patent: *Jun. 3, 2025

(54) APPARATUSES AND METHODS FOR INJECTING MEDICAMENTS

(71) Applicant: Action Medical Technologies, LLC, Conshohocken, PA (US)

(72) Inventors: Joseph B. Hoffer, Newport, PA (US); Mark W. Pursel, Grantville, PA (US); Kevin C. O'Connor, Crofton, MD (US); Andrew D. Contreras, Fairfax Station, VA (US); James P. McCans, Havertown, PA (US)

(73) Assignee: Action Medical Technologies, LLC, Conshohocken, PA (US)

( * ) Notice: Subject to any disclaimer, the term of this patent is extended or adjusted under 35 U.S.C. 154(b) by 745 days.

This patent is subject to a terminal disclaimer.

(21) Appl. No.: 17/361,912

(22) Filed: Jun. 29, 2021

(65) Prior Publication Data

US 2021/0322682 A1    Oct. 21, 2021

Related U.S. Application Data

(63) Continuation of application No. 17/212,226, filed on Mar. 25, 2021, now Pat. No. 11,065,392.

(60) Provisional application No. 62/994,448, filed on Mar. 25, 2020.

(51) Int. Cl.
| | |
|---|---|
| *A61M 5/00* | (2006.01) |
| *A61M 5/31* | (2006.01) |
| *A61M 5/32* | (2006.01) |
| *A61M 11/00* | (2006.01) |
| *A61M 39/10* | (2006.01) |

(52) U.S. Cl.
CPC ........ *A61M 5/3202* (2013.01); *A61M 5/3129* (2013.01); *A61M 11/00* (2013.01); *A61M 39/10* (2013.01); *A61M 2039/1077* (2013.01)

(58) Field of Classification Search
CPC ........ A61M 2005/3267; A61M 5/3271; A61M 5/2033; A61M 2005/208
See application file for complete search history.

(56) References Cited

U.S. PATENT DOCUMENTS

| | | |
|---|---|---|
| 3,572,336 A | 3/1971 | Hershberg |
| 3,742,948 A | 7/1973 | Post et al. |
| 4,031,893 A | 6/1977 | Kaplan et al. |
| 4,447,231 A | 5/1984 | Bekkering |
| 4,529,403 A | 7/1985 | Kamstra |
| 4,559,043 A | 12/1985 | Whitehouse et al. |

(Continued)

FOREIGN PATENT DOCUMENTS

| | | |
|---|---|---|
| CN | 102497899 A | 6/2012 |
| CN | 102665801 A | 9/2012 |

(Continued)

OTHER PUBLICATIONS

International Search Report and Written Opinion for PCT/US2021/024042 issued Jun. 28, 2021.

(Continued)

*Primary Examiner* — William R Carpenter
(74) *Attorney, Agent, or Firm* — Duane Morris LLP

(57) ABSTRACT

The disclosure relates to injectors that are configured to inject and deliver medicaments and other fluids from a syringe into a target site.

18 Claims, 27 Drawing Sheets

(56) References Cited

U.S. PATENT DOCUMENTS

| | | |
|---|---|---|
| 4,767,416 A | 8/1988 | Wolf et al. |
| 4,998,924 A | 3/1991 | Ranford |
| 5,271,744 A | 12/1993 | Kramer et al. |
| 5,320,609 A | 6/1994 | Haber et al. |
| 5,478,316 A | 12/1995 | Bitdinger et al. |
| 5,637,094 A | 6/1997 | Stewart et al. |
| 5,957,896 A | 9/1999 | Bendek et al. |
| 6,159,181 A | 12/2000 | Crossman et al. |
| 6,319,234 B1 | 11/2001 | Restelli et al. |
| 6,699,224 B2 | 3/2004 | Kirchhofer et al. |
| 6,808,507 B2 | 10/2004 | Roser |
| 7,381,201 B2 | 6/2008 | Gilbert et al. |
| 7,517,334 B2 | 4/2009 | Jacobs et al. |
| 7,717,877 B2 | 5/2010 | Lavi et al. |
| 7,905,352 B2 | 3/2011 | Wyrick |
| 7,931,618 B2 | 4/2011 | Wyrick |
| 8,123,724 B2 | 2/2012 | Gillespie, III |
| 8,187,224 B2 | 5/2012 | Wyrick |
| 8,313,463 B2 | 11/2012 | Barrow et al. |
| 8,343,103 B2 | 1/2013 | Moser |
| 8,460,245 B2 | 6/2013 | Guillermo et al. |
| 8,491,530 B2 | 7/2013 | Maritan |
| 8,529,499 B2 | 9/2013 | Matusch |
| 8,529,510 B2 | 9/2013 | Giambattista et al. |
| 8,679,061 B2 | 3/2014 | Julian et al. |
| 8,696,625 B2 | 4/2014 | Carrel et al. |
| 8,845,594 B2 | 9/2014 | Jennings |
| 9,017,293 B2 | 4/2015 | Edhouse et al. |
| 9,044,553 B2 | 6/2015 | James et al. |
| 9,186,459 B2 | 11/2015 | Bechmann et al. |
| 9,216,256 B2 | 12/2015 | Olson et al. |
| 9,242,044 B2 | 1/2016 | Markussen |
| 9,265,886 B2 | 2/2016 | Wyrick |
| 9,283,326 B2 | 3/2016 | Kemp et al. |
| 9,364,617 B2 | 6/2016 | Riedel |
| 9,421,337 B2 | 8/2016 | Kemp et al. |
| 9,427,531 B2 | 8/2016 | Hourmand et al. |
| 9,486,582 B2 | 11/2016 | Abry et al. |
| 9,579,471 B2 | 2/2017 | Carrel et al. |
| 9,827,381 B2 | 11/2017 | Hourmand et al. |
| 10,058,654 B2 | 8/2018 | Gabrielsson |
| 10,525,201 B2 | 1/2020 | Brunnberg et al. |
| 11,065,392 B1 * | 7/2021 | Hoffer ............... A61M 5/3129 |
| 2001/0056263 A1 | 12/2001 | Alchas et al. |
| 2003/0036724 A1 | 2/2003 | Vetter et al. |
| 2003/0050609 A1 | 3/2003 | Sams |
| 2006/0184115 A1 | 8/2006 | Saied |
| 2006/0189938 A1 | 8/2006 | Hommann et al. |
| 2010/0016793 A1 | 1/2010 | Jennings et al. |
| 2010/0298768 A1 | 11/2010 | Halili, Jr. et al. |
| 2012/0101475 A1 | 4/2012 | Wilmot et al. |
| 2012/0123350 A1 | 5/2012 | Giambattista et al. |
| 2012/0209192 A1 | 8/2012 | Alexandersson |
| 2013/0123710 A1 | 5/2013 | Ekman et al. |
| 2013/0190721 A1 | 7/2013 | Kemp et al. |
| 2013/0310759 A1 | 11/2013 | Hourmand et al. |
| 2014/0088512 A1 | 3/2014 | Quinn |
| 2014/0135705 A1 | 5/2014 | Hourmand et al. |
| 2014/0228769 A1 | 8/2014 | Karlsson et al. |
| 2015/0011975 A1 | 1/2015 | Anderson et al. |
| 2015/0025474 A1 | 1/2015 | Riedel et al. |
| 2015/0246181 A1 | 9/2015 | Fourt et al. |
| 2015/0250951 A1 | 9/2015 | Karlsson et al. |
| 2015/0265782 A1 | 9/2015 | Riedel et al. |
| 2015/0283323 A1 | 10/2015 | Young et al. |
| 2016/0008542 A1 | 1/2016 | Hirschel et al. |
| 2016/0008546 A1 | 1/2016 | Rekaya et al. |
| 2017/0136186 A1 | 5/2017 | Marsh et al. |
| 2018/0099095 A1 | 4/2018 | Standley et al. |
| 2018/0296764 A1 | 10/2018 | Davies et al. |
| 2019/0143050 A1 | 5/2019 | Montgomery et al. |
| 2019/0240409 A1 | 8/2019 | Holmqvist |

FOREIGN PATENT DOCUMENTS

| | | |
|---|---|---|
| CN | 103249443 A | 8/2013 |
| CN | 103945881 A | 7/2014 |
| JP | 2010532243 | 10/2010 |
| JP | 2013529521 | 7/2013 |
| JP | 2015519135 | 7/2015 |
| JP | 2015530170 | 10/2015 |
| WO | 2012000873 A1 | 1/2012 |
| WO | 2018125629 A1 | 7/2018 |
| WO | 2019158549 A1 | 8/2019 |

OTHER PUBLICATIONS

Extended European Search Report for European Patent Application No. 21774692.4 issued Aug. 22, 2023, 8 pages.

\* cited by examiner

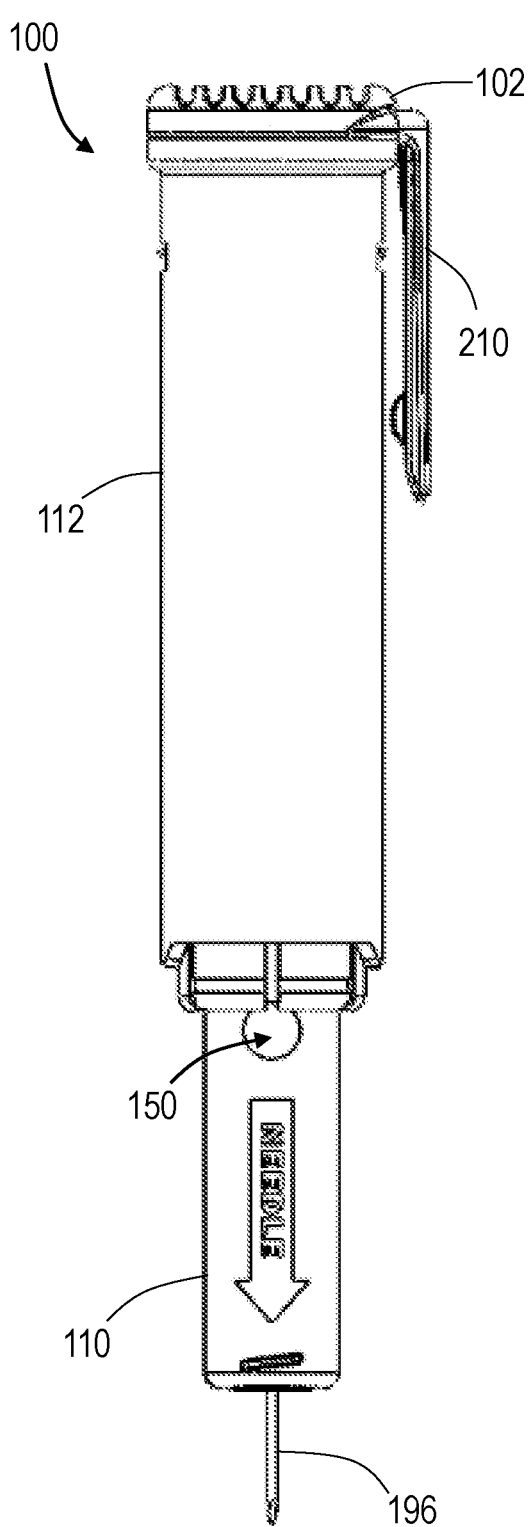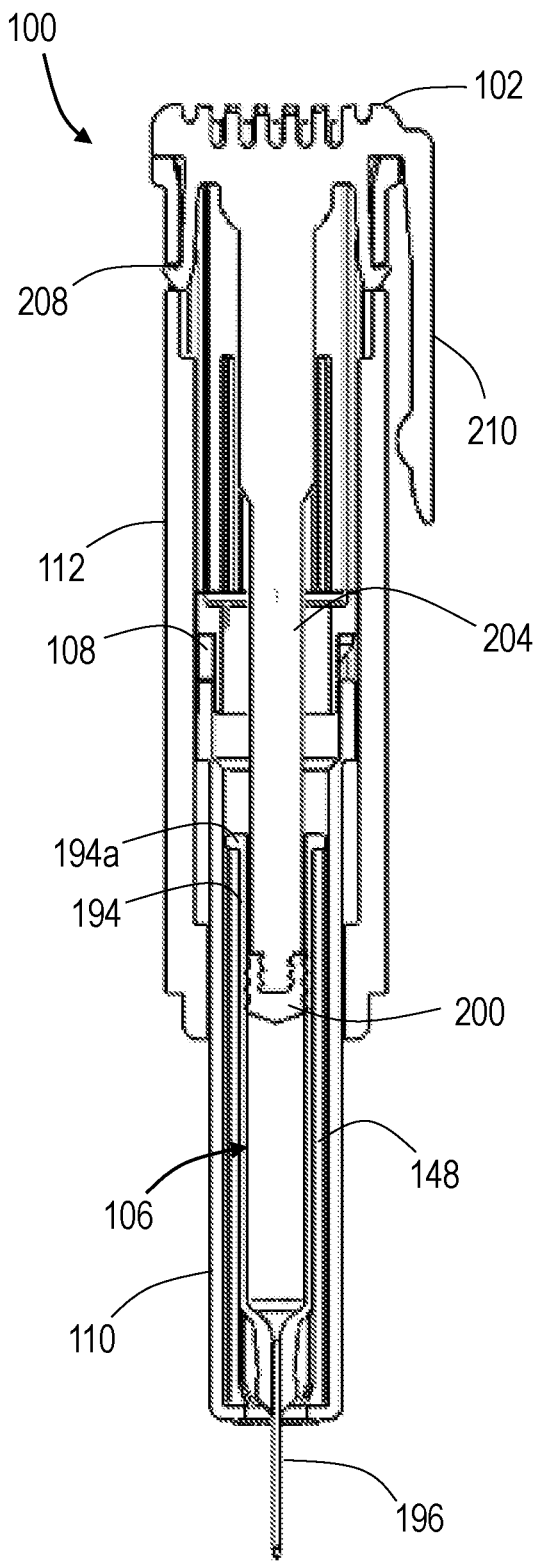
FIG. 13A
FIG. 13B

APPARATUSES AND METHODS FOR INJECTING MEDICAMENTS

CROSS-REFERENCE TO RELATED APPLICATION

This application is a continuation application of U.S. patent application Ser. No. 17/212,226, filed Mar. 25, 2021, which claims the benefit of priority to U.S. Provisional Patent Application No. 62/994,448, filed on Mar. 25, 2020, the entire disclosure of each of which is expressly incorporated herein by reference in its entirety.

FIELD

The invention relates to injectors for medicaments and other fluids. Specifically, to injectors configured to inject a medicament and other fluids from a syringe.

BACKGROUND

Many methods are used to inject medicaments and other fluids into a target site. These include syringes, auto-injectors, and drug pumps. The medicament can be injected at a variety of depths. For example, the medicament can be injected into the epidermis, the dermis, the subcutaneous region, or into the muscles (intramuscular). Medicament or other fluids can also be delivered intravenously, intraosseusly, and/or to other parts of the body such as into the eye. Some of these devices are specifically intended for at home use by a patient. These devices can be used to deliver a variety of medicaments. For example, the injectors can be used for the delivery of epinephrine to patients who are at risk of anaphylaxis. Such devices include the ANAPEN™ injector sold by Lincoln Medical Ltd. of the United Kingdom and the EPIPEN® injector sold by Mylan Inc. of Pennsylvania.

Many injectors use powerful springs to drive a plunger rod into a pre-filled syringe and inject the medicament into the tissue while pushing the injector into the side of the leg or other body location. Some of these injectors have the advantage of visually shielding the needle before and/or after use, thereby benefiting patients who have a fear of needles. Present injectors can contain more than twenty-six parts, including electronics and even speakers, and may be complicated to assemble due to the amount and complexity of the parts, which contributes to high prices for the user. The additional parts also increase the chance of failure of these complex devices.

SUMMARY

In one or more embodiments, an injector includes an outer tubular sleeve defining a longitudinal axis. In one or more embodiments, the injector includes a cam disposed within the outer sleeve. In one or more embodiments, the injector includes an inner sleeve disposed partially within the outer sleeve and a first end of the inner sleeve is configured to engage with the cam. In one or more embodiments, the injector includes a syringe comprising a barrel, a needle mounted to an end of the barrel, a plunger, and a seal slidably mounted in the barrel. In some embodiments, the plunger is engaged with the outer sleeve in a fixed spatial relationship such that the plunger and outer sleeve translate as a unit throughout operation of the injector. In some embodiments, the outer sleeve is disposed and configured for axial translation relative to the inner sleeve from a first configuration. In some embodiments, the inner sleeve is configured to extend from the outer sleeve a first distance to a second configuration in which the inner sleeve extends from the outer sleeve a second distance that is less than the first distance. In some embodiments, the inner sleeve is further configured to extend from the outer sleeve a to a third configuration in which the inner sleeve extends from the outer sleeve a third distance that is greater than the second distance and the cam rotates from a first position to a second position thereby restricting the inner sleeve from axially translating with respect to the outer sleeve.

In one or more embodiments, a medicament delivery system includes an injector. In some embodiments, the injector includes an outer tubular sleeve defining a longitudinal axis. In some embodiments, the injector includes a cam disposed within the outer sleeve. In some embodiments, the injector includes an inner sleeve disposed partially within the outer sleeve and a first end of the inner sleeve is configured to engage with the cam. In some embodiments, the injector includes a syringe comprising a barrel, a needle mounted to an end of the barrel, a plunger, and a seal slidably mounted in the barrel. In some embodiments, the plunger is engaged with the outer sleeve in a fixed spatial relationship such that the plunger and outer sleeve translate as a unit throughout operation of the injector. In some embodiments, the outer sleeve is disposed and configured for axial translation relative to the inner sleeve from a first configuration. In some embodiments, the inner sleeve is configured to extend from the outer sleeve a first distance to a second configuration in which the inner sleeve extends from the outer sleeve a second distance that is less than the first distance. In some embodiments, the inner sleeve is further configured to extend from the outer sleeve a to a third configuration in which the inner sleeve extends from the outer sleeve a third distance that is greater than the second distance and the cam rotates from a first position to a second position thereby restricting the inner sleeve from axially translating with respect to the outer sleeve. In one or more embodiments, the medicament delivery system includes an adapter configured to couple to a second end of the inner sleeve.

A variety of additional aspects will be set forth in the description that follows. The aspects can relate to individual features and to combination of features. It is to be understood that both the foregoing general description and the following detailed description are exemplary and explanatory only and are not restrictive of the broad inventive concepts upon which the embodiments disclosed herein are based.

BRIEF DESCRIPTION OF THE DRAWINGS

The features of the devices and methods provided herein will be more fully disclosed in, or rendered obvious by, the following detailed description of the preferred embodiment of the invention, which is to be considered together with the accompanying drawings wherein like numbers refer to like parts.

FIGS. 13A and 13B are side and side cross-sectional views, respectively, of the injector of FIG. 1 after extending the needle of syringe from the inner sleeve of the injector to insert the needle in a target site.

DETAILED DESCRIPTION

Figure 1:
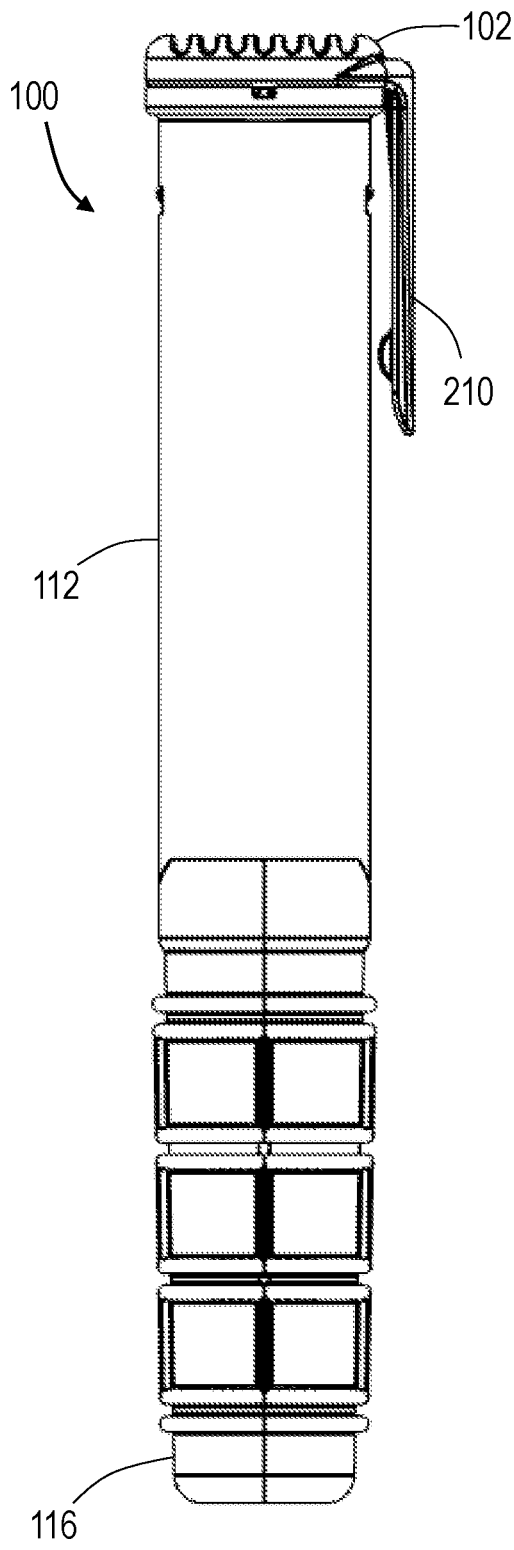
FIG. 1 is a side view of an injector according to one embodiment described herein.

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively or operably connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures. The terms "medicament" or "drug" as used herein refers to any substance for delivery to a target. For example, these terms include anticoagulants, vaccines, biologics, and any injectable fluid.

The present disclosure describes an injector for injecting medicament into a target site. The injector provides for easy use by a medical professional, caregiver, or self-administration by patient and is configured for reliable use after being stored for long periods of time. In addition, because the injector utilizes a low number of parts, it is inexpensive and easy to manufacture. The injectors described herein can be used to deliver, for example, epinephrine, ketamine, atropine, diazepam, or naloxone.

Figure 2:
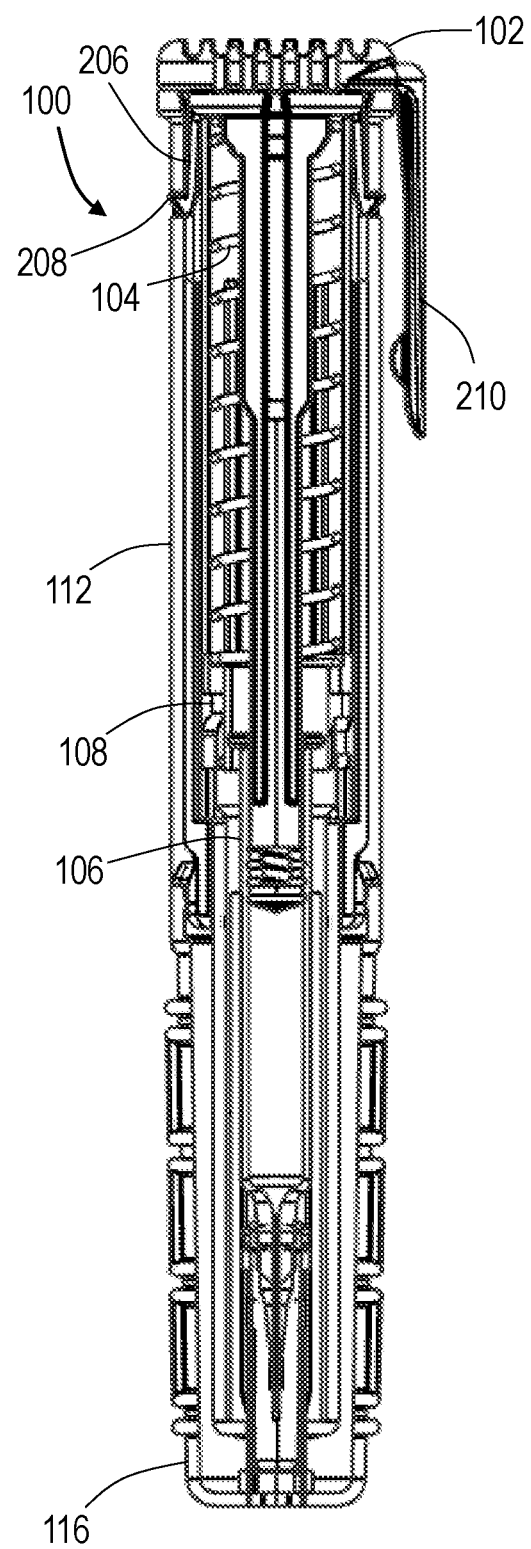
FIG. 2 is a side cross-sectional view of the injector of FIG. 1.
Figure 3:
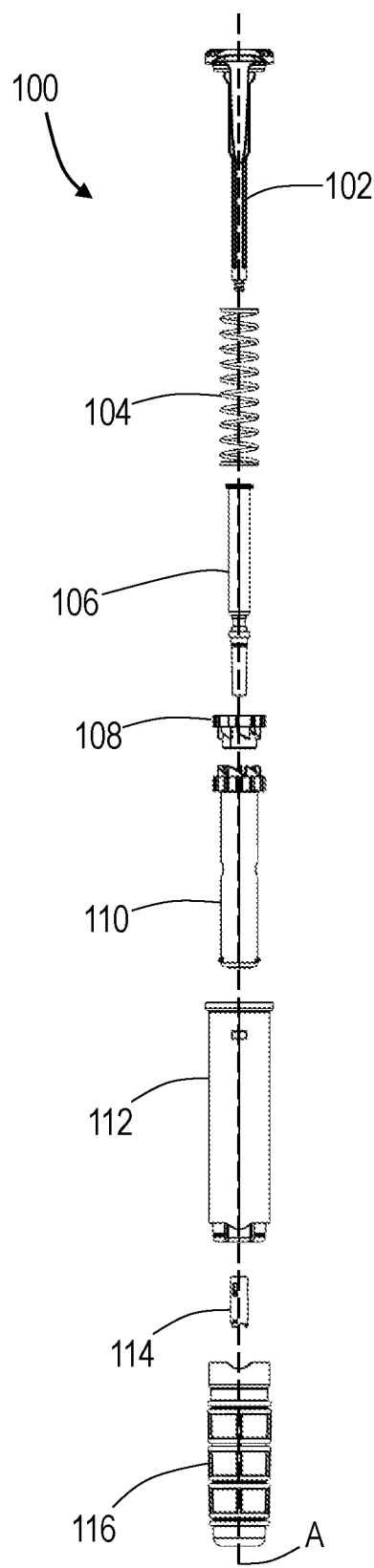
FIG. 3 is an exploded side view of the injector of FIG. 1.

FIG. 1 shows a side view of an injector 100 according to one embodiment, and FIG. 2 shows a side cross-sectional view of the injector 100. FIG. 3 shows an exploded view of the injector 100. The injector 100 includes a plunger 102, a biasing member 104, a syringe 106, a cam 108, an inner sleeve 110, an outer sleeve 112, a needle cover engagement member 114, and a cap 116. As shown in FIG. 2, the syringe 106 is disposed in a chamber defined by the inner sleeve 110, the outer sleeve 112, and the cap 116. As described in further detail herein, when a user desires to inject the medicament contained in the syringe 106, the user removes the cap 116 and selectively deploys the needle of the syringe 106 to inject the medicament.

Figure 4:
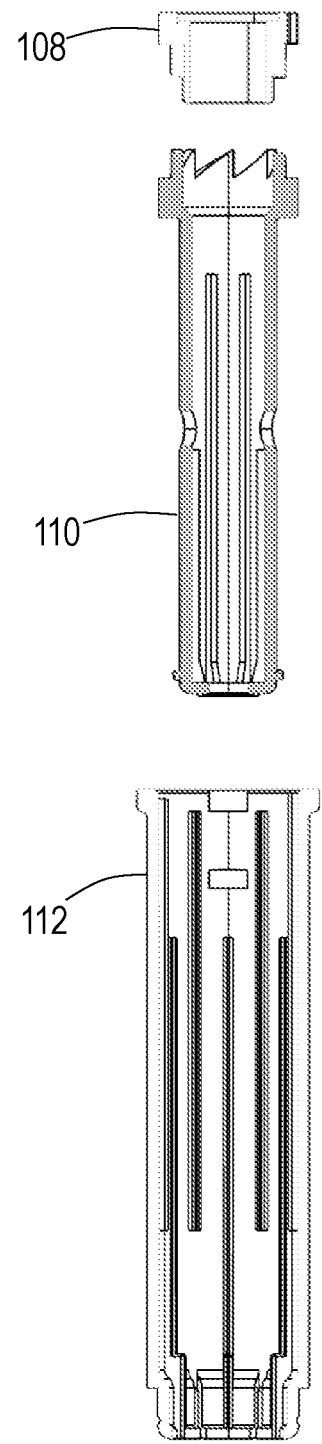
FIG. 4 is an exploded side view of the outer sleeve, inner sleeve, and cam of the injector of FIG. 1.

FIG. 4 shows an exploded view of the cam 108, the inner sleeve 110, and the outer sleeve 112. As described in further detail herein, the cam 108, the inner sleeve 110, and the outer sleeve 112 work together to: (i) cover the needle of the syringe prior to insertion of the needle in the injection site; (ii) provide audible (e.g., a "click") and/or tactile feedback upon completion of injection of the medicament; and (iii) cover the needle of the syringe after completion of injection to prevent inadvertent needle stick injuries.

Figure 5A:
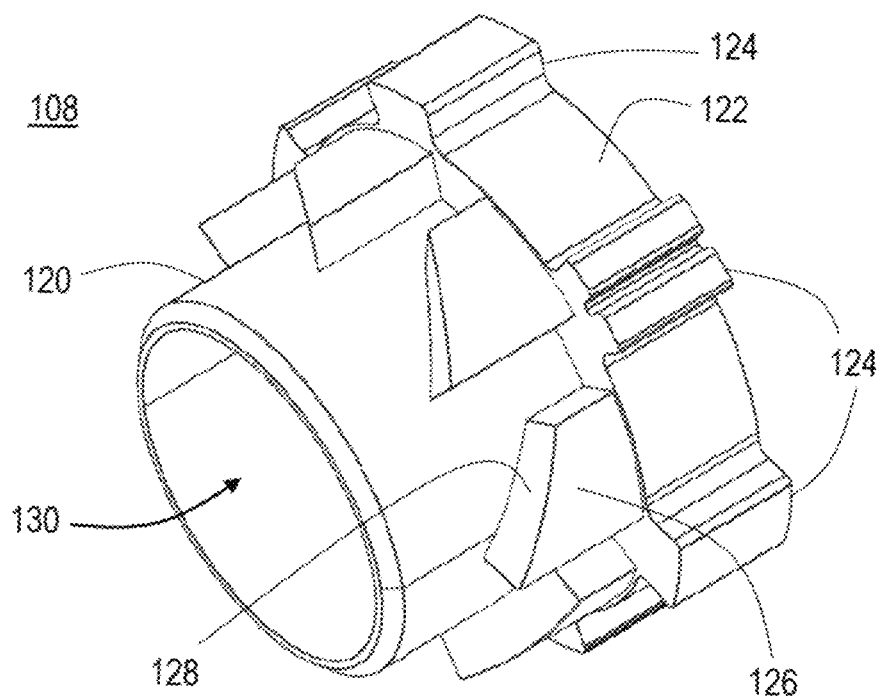
FIG. 5A is a perspective view of the cam of the injector of FIG. 1.
Figure 5B:
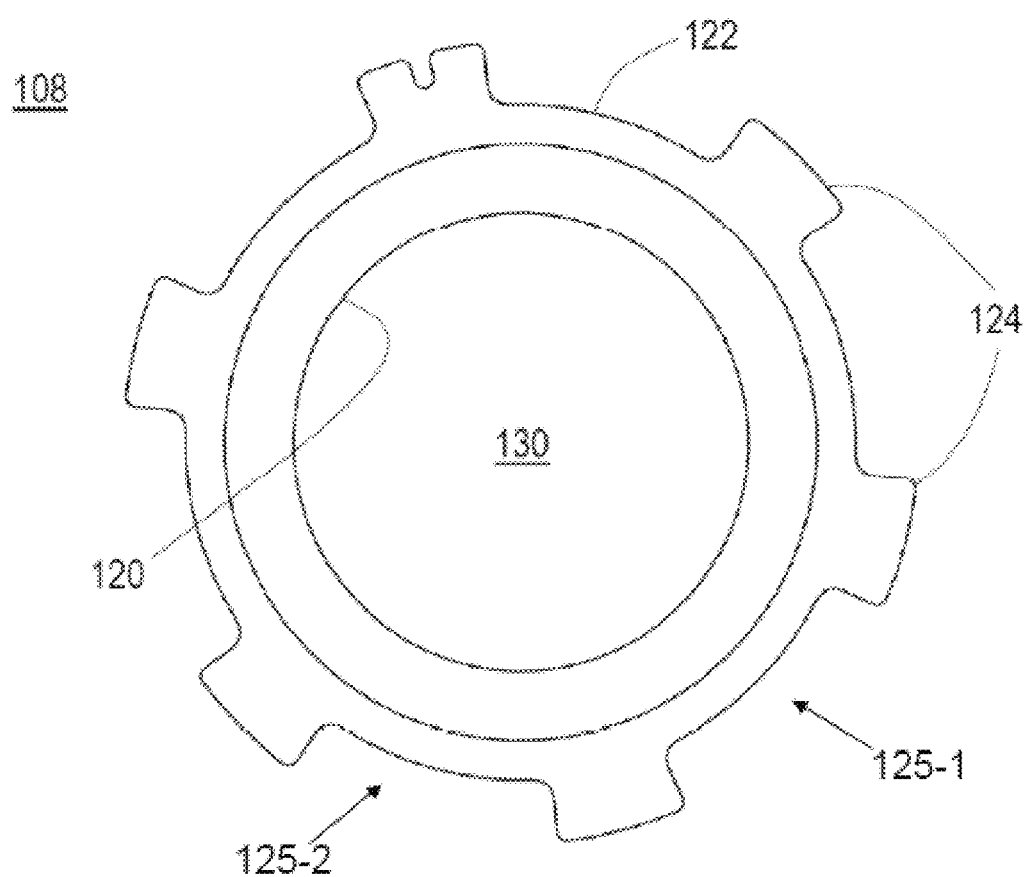
FIG. 5B is an end view of the cam of FIG. 5A.

As shown in FIG. 2, the cam 108 is disposed within the outer sleeve 112 and is configured for axial translation within the outer sleeve 112. As described in more detail herein, the cam 108 is also configured to rotate within the outer sleeve 112 during use of the injector 100. FIG. 5A shows a perspective view of the cam 108 and FIG. 5B shows an end view of the cam 108. The cam 108 includes a cylindrical body 120 and a ring 122 extending from the cylindrical body 120 and having a larger outer diameter than the cylindrical body 120—for example, at one end of the cylindrical body 120. The cam 108 further includes a plurality of protrusions 124 extending radially outward from the ring 122 that define a first set of recesses 125-1 and a second set of recesses 124-2 such that the first and the second sets of recesses are alternately and circumferentially disposed around the cam 108 between the plurality of protrusions 124. The protrusions 124 are circumferentially spaced around the ring 122. The protrusions 124 are configured to guide translation and rotation of the cam 108 within the outer sleeve 112 during use, as described herein. The cam 108 further includes cam elements 126 extending from the outside of the cylindrical body 120—for example, adjacent to the ring 122. The cam elements 126 each include a cam face 128. The cam faces 128 are angled relative to the circumference of the cylindrical body 120 such that engagement with corresponding faces on the inner sleeve 110 imparts a circumferential force on the cam 108 that causes the cam 108 to rotate at desired times during operation of the injector 100, as described in detail herein. The cylindrical body 120 defines an aperture 130 to allow for the passage of the plunger 102.

Figure 6:
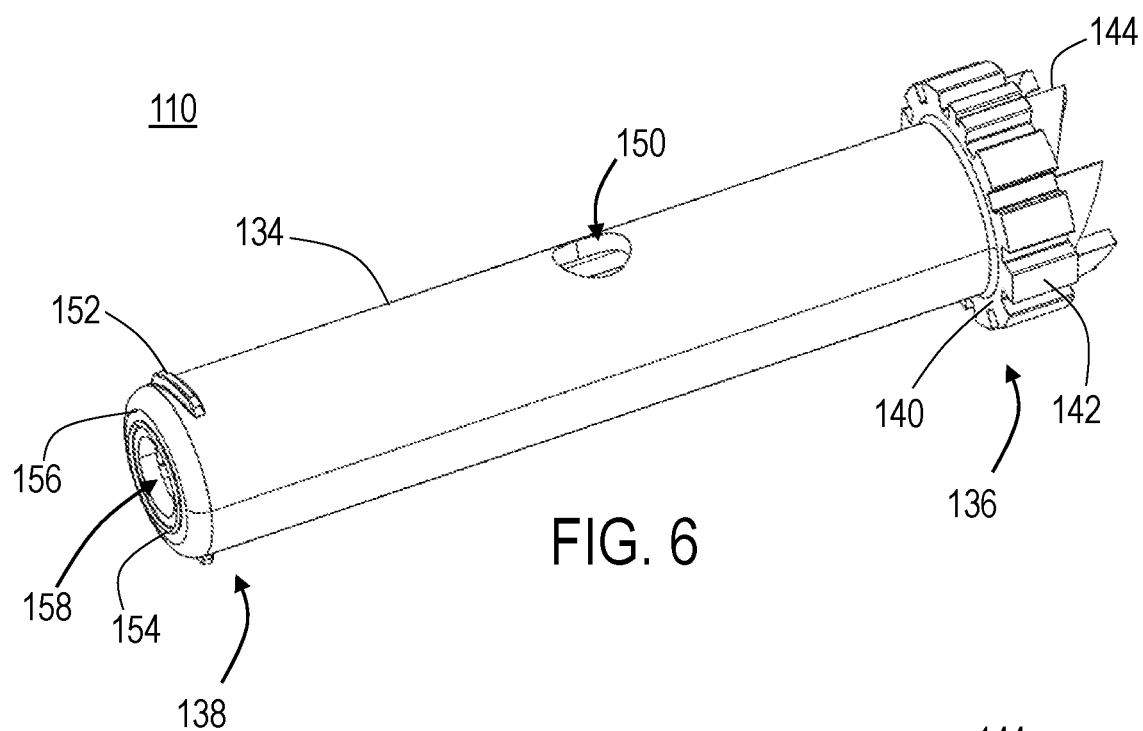
FIG. 6 is a perspective view of the inner sleeve of the injector of FIG. 1.
Figure 7:
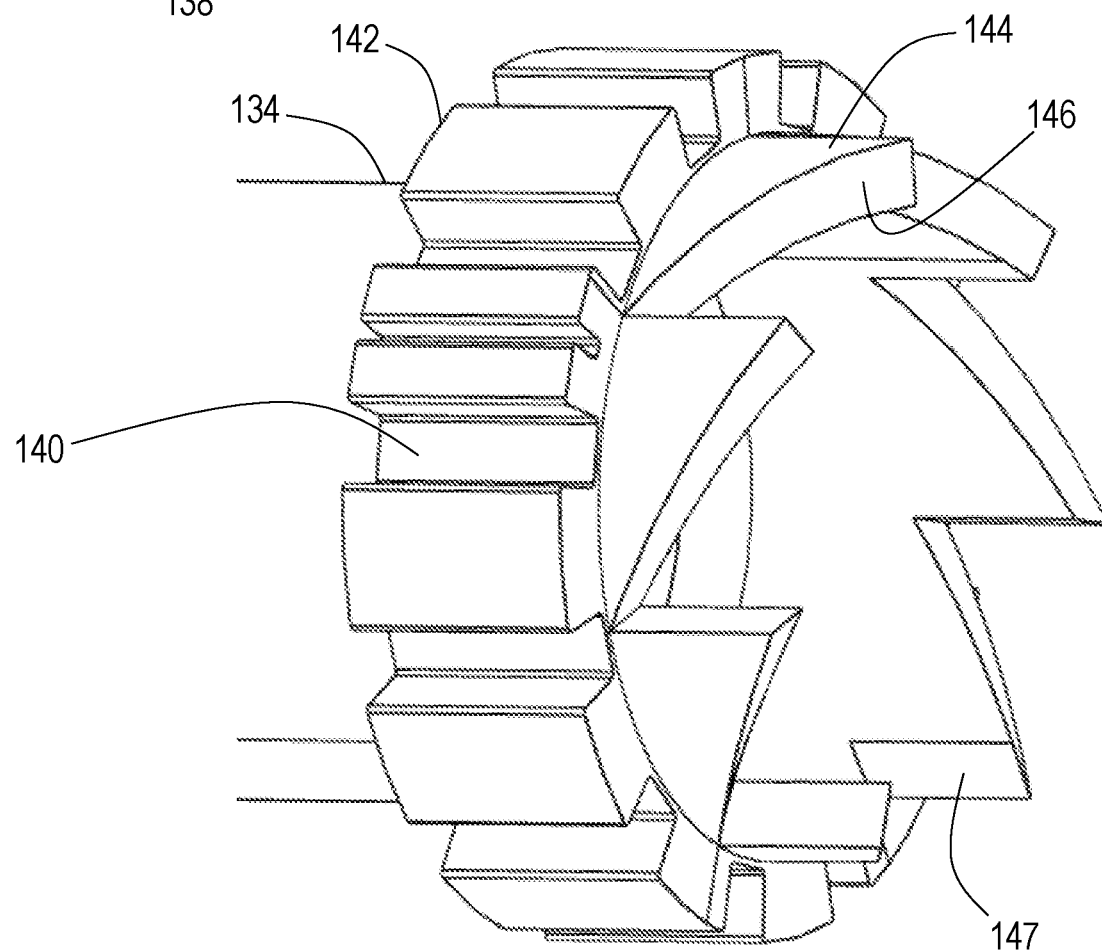
FIG. 7 is a detail perspective view of an end of the inner sleeve of FIG. 6.
Figure 8:
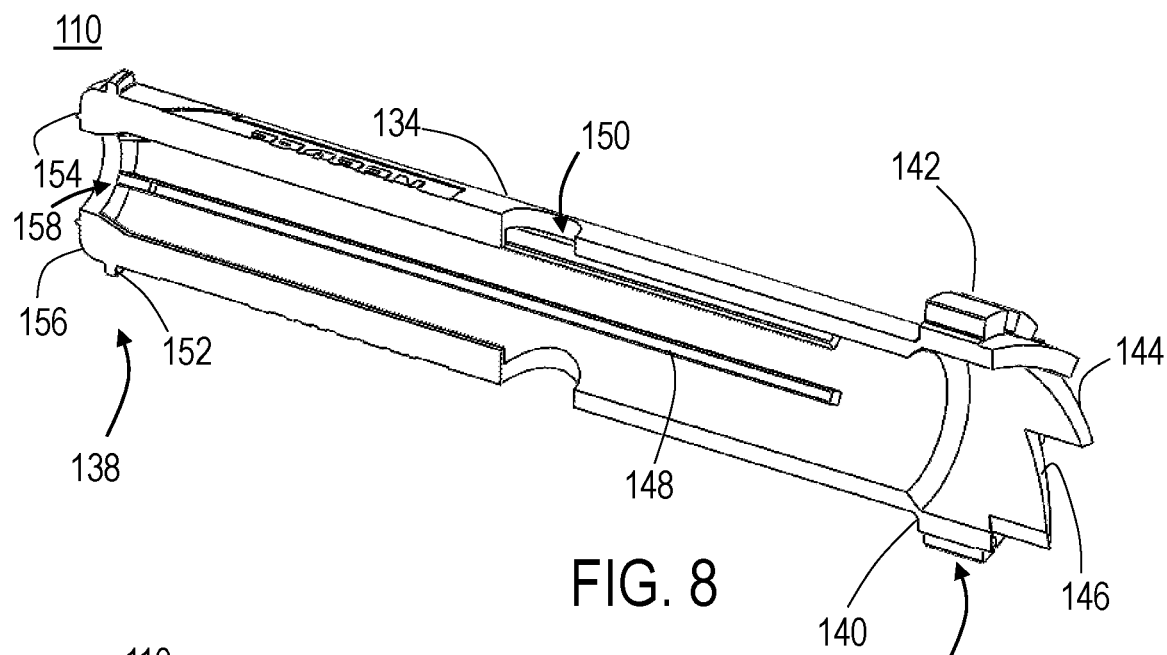
FIG. 8 is a cross-sectional perspective view of the inner sleeve of FIG. 6.
Figure 9:
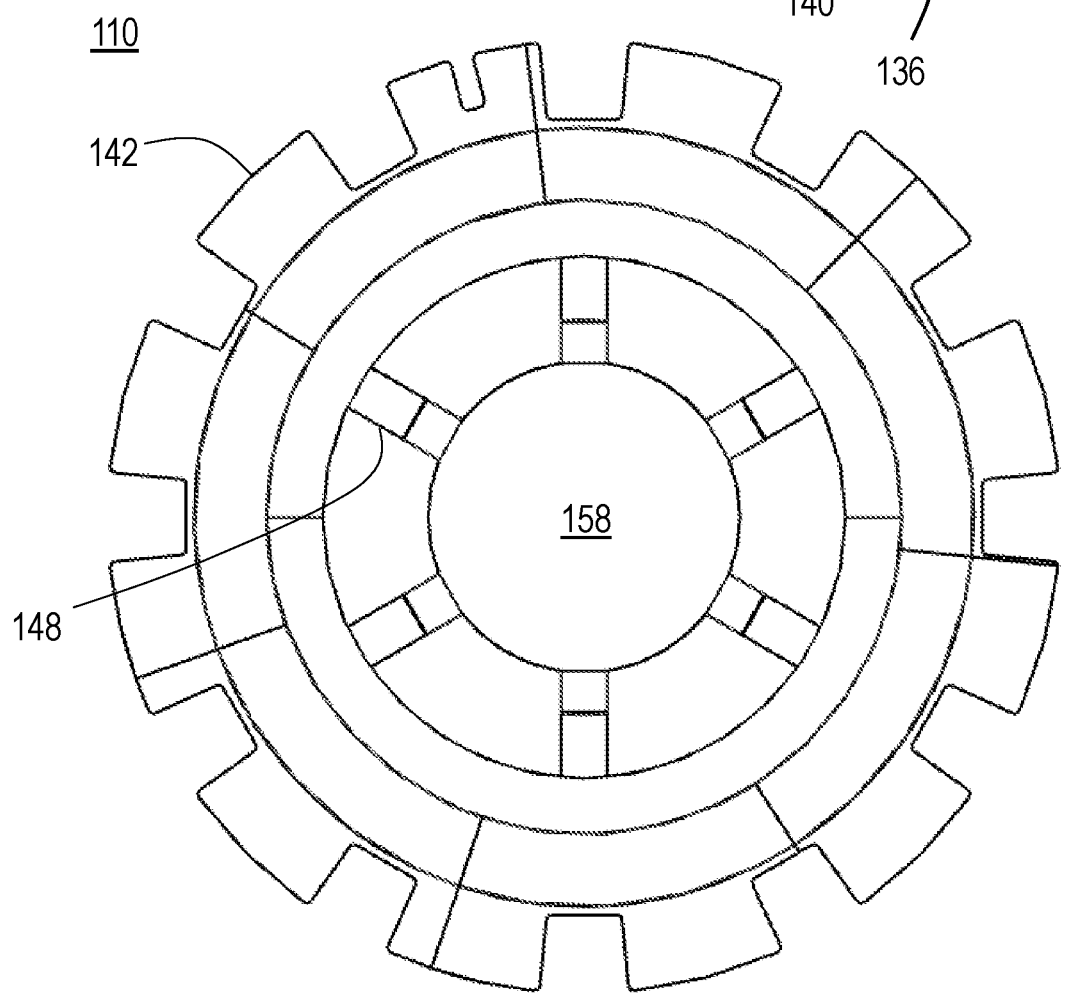
FIG. 9 is an end view of the inner sleeve of FIG. 6.
Figure 37:
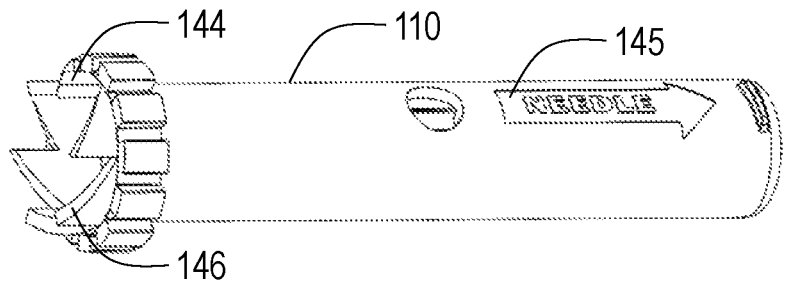
FIG. 37 is a perspective view of an alternative embodiment of the inner sleeve of the injector of FIG. 1.

FIG. 6 shows a perspective view of the inner sleeve 110, and FIG. 37 shows a perspective view of an alternative inner sleeve 110. FIG. 7 shows a detailed perspective view of an end of the inner sleeve 110. FIG. 8 shows a cross-sectional perspective view of the inner sleeve 110. FIG. 9 shows an end view of the inner sleeve 110. The inner sleeve 110 includes a cylindrical body 134 extending from a first end 136 to a second end 138. The inner sleeve 110 further includes a ring 140 extending from the cylindrical body 134 and having a larger outer diameter than the cylindrical body 134 and a plurality of projections 142 extending radially outward from the ring 140—for example, at the first end 136 of the cylindrical body 134. As described in further detail herein, the projections 142 are configured to restrict rotation of the inner sleeve 110 in the outer sleeve 112 during operation of the injector 100. The inner sleeve 110 further includes a plurality of cam teeth 144 extending from the first end 136 of the cylindrical body 134. The cam teeth 144 each include an angled face 146 (i.e., angled relative to the circumference of the cylindrical body 134) configured to engage a cam face 128 of the cam elements 126 of the cam 108 during operation of the injector 100 to cause rotation of the cam 108, as described in detail herein. As shown in FIGS. 8 and 9, the inner sleeve 110 further includes a plurality of ribs 148 extending radially inward from the cylindrical body 134 and extending longitudinally along the cylindrical body 134. The ribs 148 locate and retain the syringe 106 in position when it is disposed within the cylindrical body 134 of the inner sleeve 110. The inner sleeve 110 further includes a window 150 extending through the inner sleeve 110 that allows a user to view the contents of the syringe 106 before injection (e.g., after removal of the cap 116). It is noted that the inner sleeve 110 illustrated in FIG. 37 includes one or more of the same or similar features as the inner sleeve 110 illustrated in FIG. 6, and the inner sleeve 110 of FIG. 37 is provided to show that inner sleeve 110 may include any number of cam teeth 144, such as six cam teeth, to correspond to the number of cam elements 126 of cam 108.

The inner sleeve 110 further includes ridges 152 extending from the cylindrical body 134 at the second end 138 of the cylindrical body 134. The ridges 152 each extend partially around the circumference of the inner sleeve 110 and include faces that are disposed at an acute angle with respect to a circumference of the cylindrical body 134. As described in further detail herein, the ridges 152 allow for the connection of adapters to the injector 100 by engaging with threads of the adapters.

The inner sleeve 110 further includes a rib 154 extending from a front face 156 of the inner sleeve 110 and extending circumferentially around an aperture 158 through the front face 156. The aperture 158 is configured to allow the passage of the needle of the syringe 106 therethrough during operation of the injector. As described in further detail herein, the rib 154 is configured to engage a diaphragm of an adapter coupled to the injector 100 to seal the inner sleeve 110 to the adapter.

Figure 10:
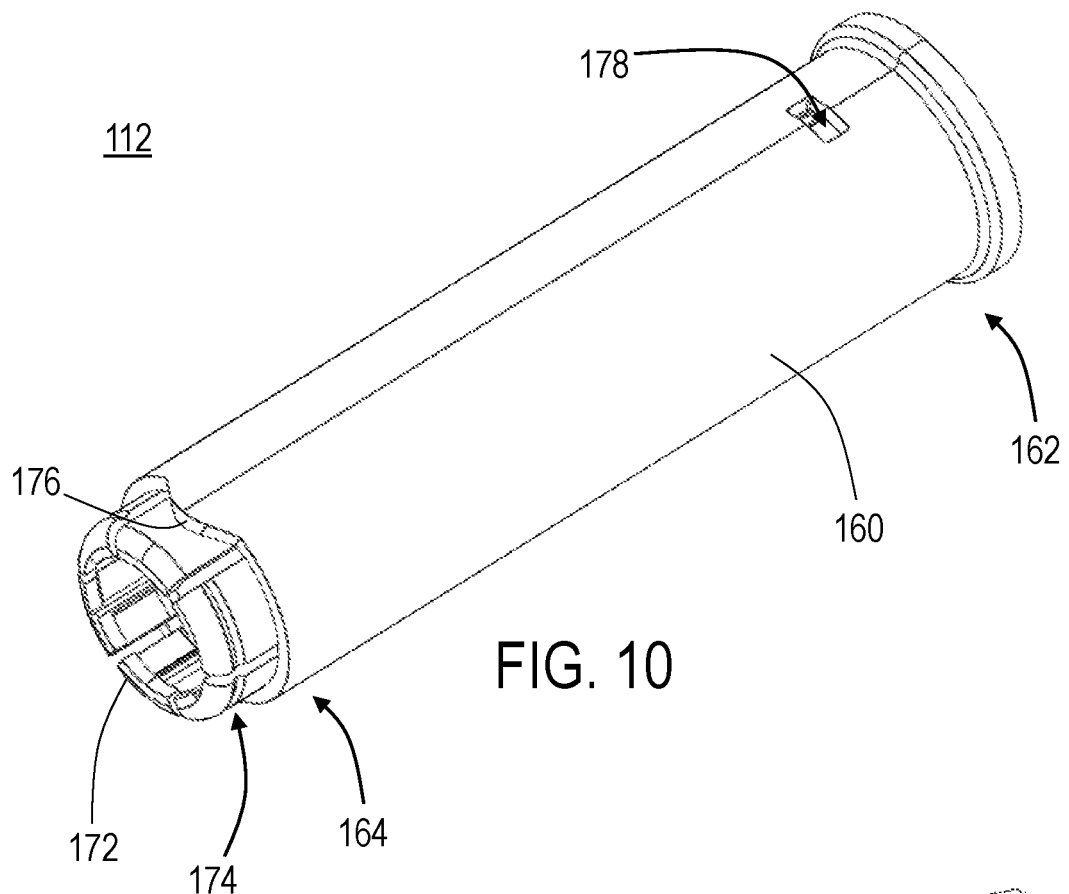
FIG. 10 is a perspective view of the outer sleeve of the injector of FIG. 1.
Figure 11:
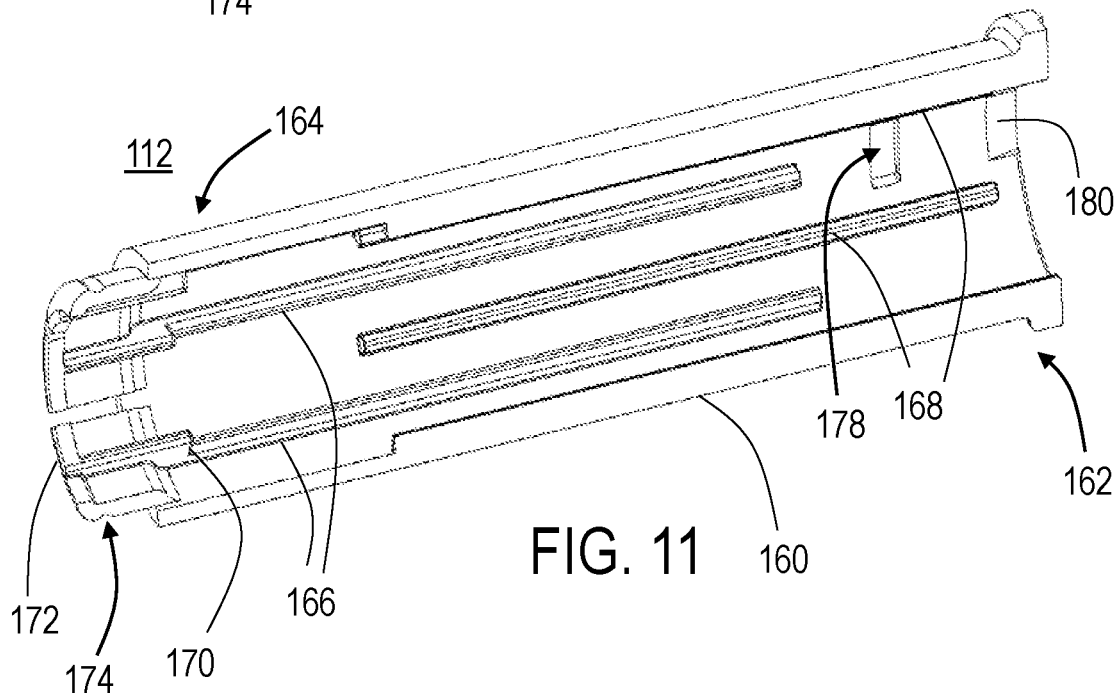
FIG. 11 is a cross-sectional perspective view of the outer sleeve of FIG. 10.

FIG. 10 shows a perspective view of the outer sleeve 112, and FIG. 11 shows a cross-sectional perspective view of the outer sleeve 112. The outer sleeve 112 includes a cylindrical body 160 for housing the inner sleeve 110, the cam 108, and the syringe 106. The cylindrical body 160 extends from a first end 162 to a second end 164. The outer sleeve 112 includes a plurality of first ribs 166 and a plurality of second ribs 168 each extending inward from the cylindrical body 160. The first ribs 166 extend from the second end 164 and toward the first end 162, however, the first ribs 166 do not extend all the way to the first end 162. As described further herein, this allows the cam 108 to rotate within the outer sleeve 112 at a specific stage of operation of the injector 100, specifically at completion of injection of the medicament. The second ribs 168 are spaced apart from the second end 164. As described in further detail herein, this allows the cam 108 to rotate within the outer sleeve 112 at a specific stage of operation of the injector 100, specifically after removal of the injector 100 from the injection site and extension of the inner sleeve 110. In various embodiments, the first 166 and second 168 ribs extend parallel to the longitudinal axis A of the injector 100 (shown in FIG. 3). The first ribs 166 define a shoulder 170 configured to engage the ring 140 on the inner sleeve 110, when the inner sleeve 110 is extended, to locate the inner sleeve 110.

The outer sleeve 112 further includes fingers 172 extending from the second end 164 of the cylindrical body 160. A groove 174 is defined in the outside of the fingers 172. The groove 174 is configured to receive a bead on the cap 116 to couple the cap 116 to the outer sleeve 112, as described in more detail herein. The outer sleeve 112 also includes ramped projections 176 configured to engage the cap 116 when the cap 116 is in place on the injector 100. The ramped projections 176 may extend outward from the cylindrical body 160 and along the outside of one or more of the fingers 172. The ramped projections 176 may have surfaces that are inclined relative to the longitudinal axis of the outer sleeve 112. As described in more detail herein, the inclined faces cause the cap 116 to be pushed outward, away from the first end 162 of the outer sleeve 112 when the cap 116 is twisted relative to the outer sleeve 112. The fingers 172 can flex inward (toward the longitudinal axis A) during installation and removal of the cap 116.

The outer sleeve 112 has apertures 178 at the first end 162 configured to receive teeth of the plunger 102 to couple the plunger 102 to the outer sleeve 112, as described herein. The outer sleeve 112 also has ramps 180 at the first end 162 to provide a lead in for the teeth of the plunger 102.

Figure 18A:
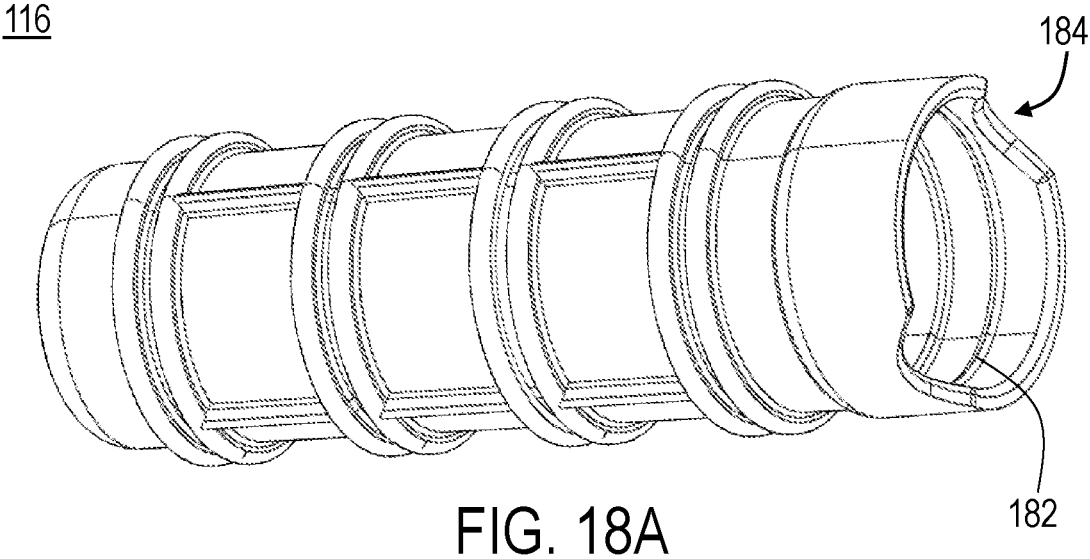
FIG. 18A is a perspective view of the cap of the injector of FIG. 1.
Figure 18B:
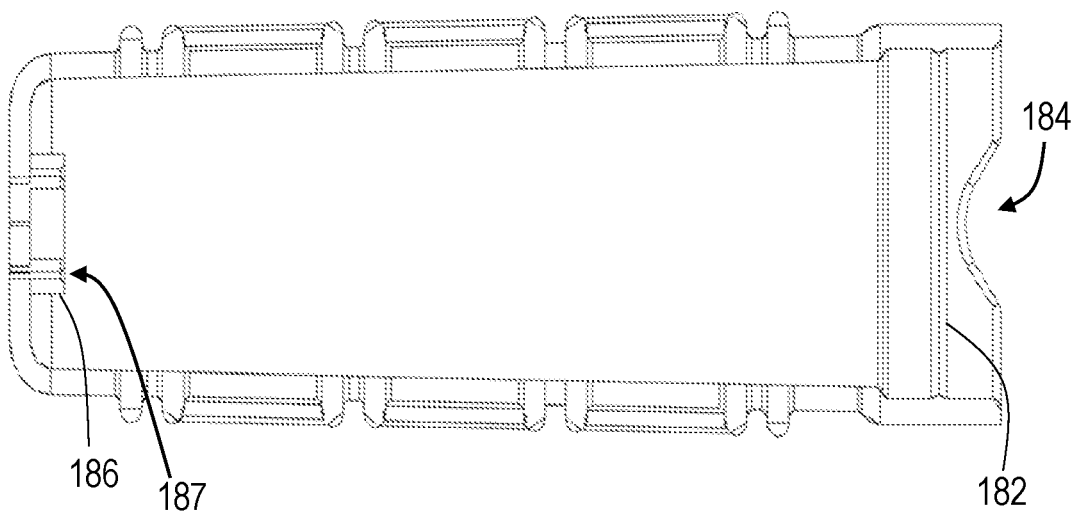
FIG. 18B is a side cross-sectional view of the cap of FIG. 18A.

FIGS. 18A and 18B show perspective and cross-sectional side views, respectively, of the cap 116. The cap 116 can include features that allow a user to grasp the cap 116 and remove it from the injector 100. The cap 116 includes a bead 182 extending circumferentially around the inside of the cap 116 to engage the groove 174 in the outer sleeve 112. The cap 116 defines recesses 184 extending into the end of the cap 116 and configured to receive the ramped projections 176 of the outer sleeve 112. When the cap is twisted by a user, the sides of the recesses 184 contact the ramped projections 176. This contact imparts an axial force on the cap 116 that pushes the cap 116 axially, way from the outer sleeve 112 to assist the user in removing the cap 116 from the injector 100. The cap 116 has a boss 186 at its bottom end. The boss 186 includes a groove 187 that is configured to receive a portion of the needle cover engagement member 114.

Figure 19:
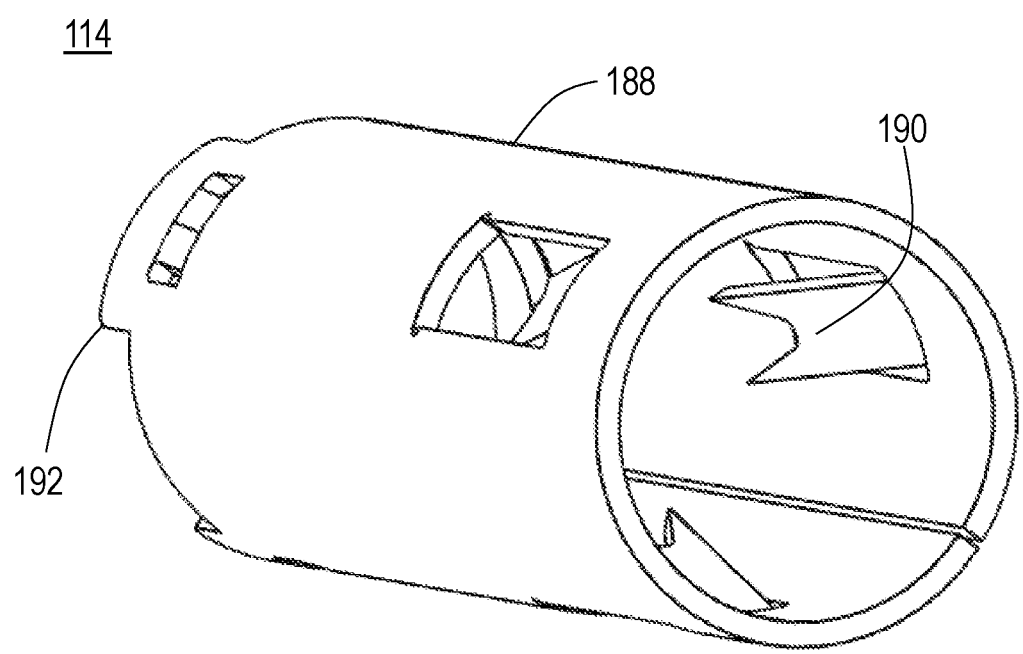
FIG. 19 is a perspective view of the needle cover engagement member of the injector of FIG. 1.

As shown in FIG. 19, the needle cover engagement member 114 includes a cylindrical body 188 and teeth 190 extending inward from the cylindrical body 188. The teeth 190 are configured to engage the needle cover of the syringe 106. The teeth 190 can be formed by pressing portions of the cylindrical body 188 inward, toward the center of the cylindrical body 188. The needle cover engagement member 114 further includes feet 192 to engage the cap 116 to couple the needle cover engagement member 114 to the cap 116. Specifically, the feet 192 engage the groove 187 in the cap 116. Hence, the removal of the cap 116 also removes the needle cover from the syringe 106.

Figure 31:
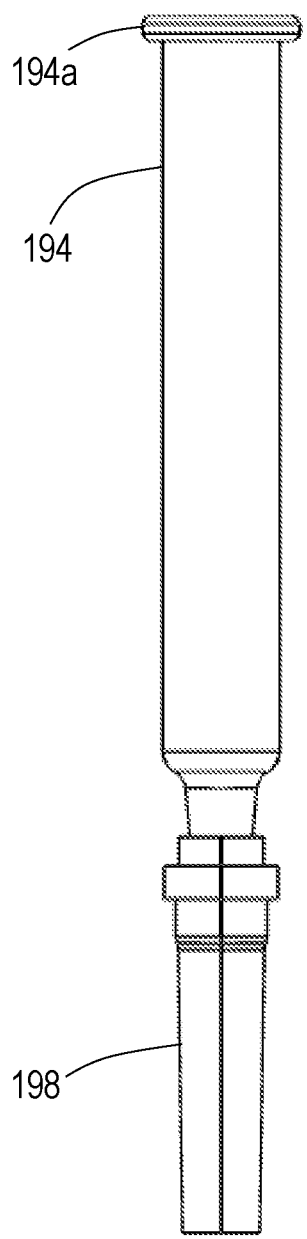
FIG. 31 is a side view of the syringe of the injector of FIG. 1.
Figure 32:
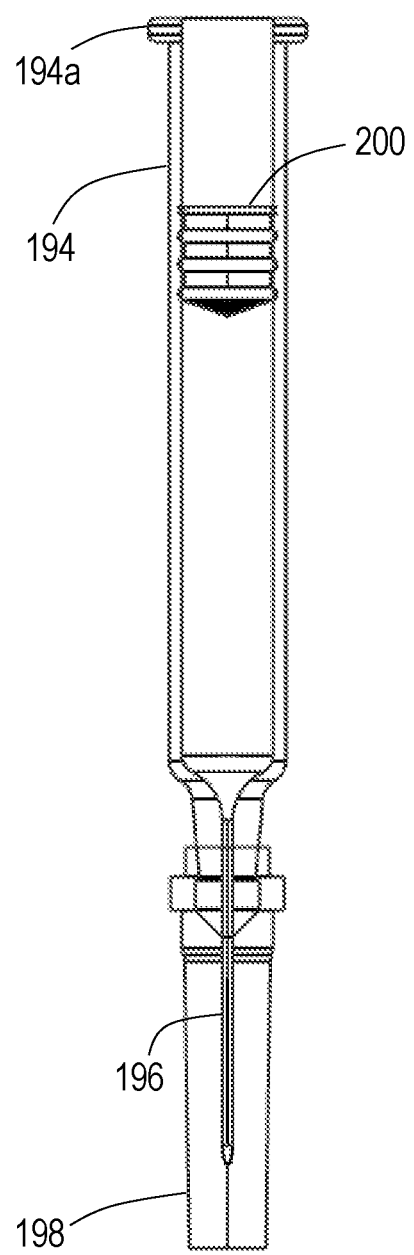
FIG. 32 is a side cross-sectional view of the syringe of FIG. 31.

FIG. 31 shows a side view of the syringe 106 and FIG. 32 shows a side cross-sectional view of the syringe 106. The syringe 106 may be pre-filled with a medicament and includes a barrel 194, a needle 196, a needle cover 198, and a plunger seal 200. The barrel 194 can be a glass barrel, such as those constructed from straight cane glass. Alternatively, the barrel 194 can be constructed of a polymeric material. The barrel 194 can be coated with a material to reduce chemical interactions between the barrel 194 and the medicament. The needle 196 is mounted at the distal end of the barrel 194 and defines a lumen through which medicament can be delivered from the barrel 194 to the target site. The needle 196 can be attached to the barrel 194 using any appropriate method, such as staking and adhesives. The plunger seal 200 is disposed within the barrel 194 and is configured for axial translation within the barrel 194. The plunger seal 200 can be constructed of an elastomeric material and provide a seal against the inner wall of the barrel 194 to maintain the sterility of the medicament prior to use.

Figure 20:
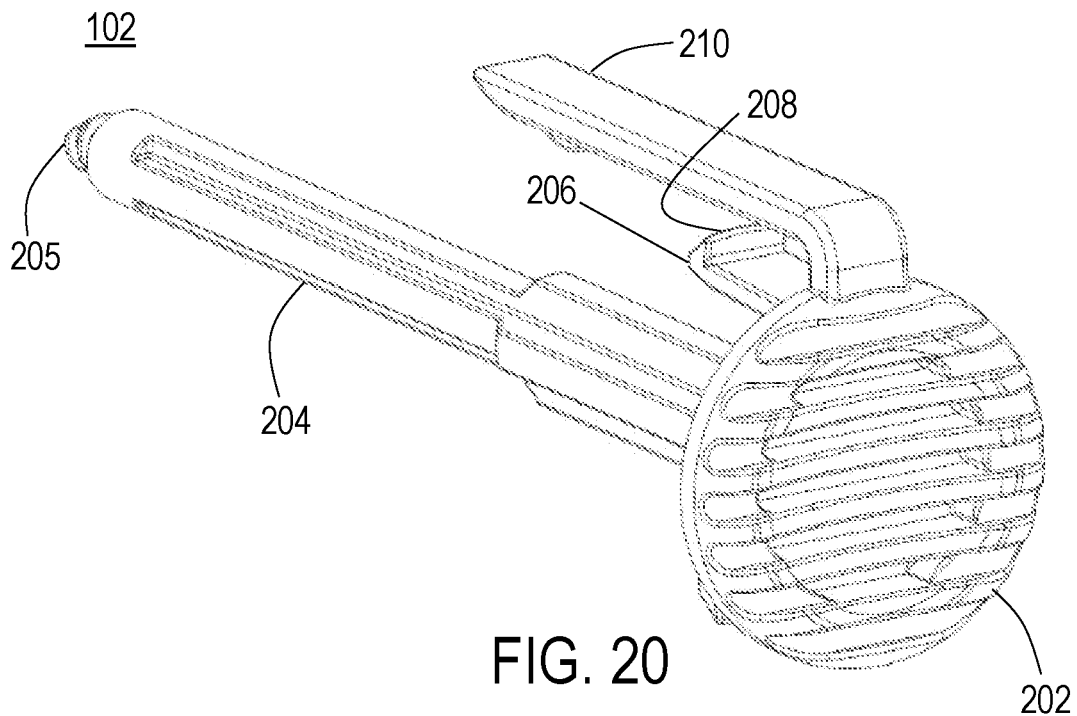
FIG. 20 is a perspective view of the plunger of the injector of FIG. 1.
Figure 38:
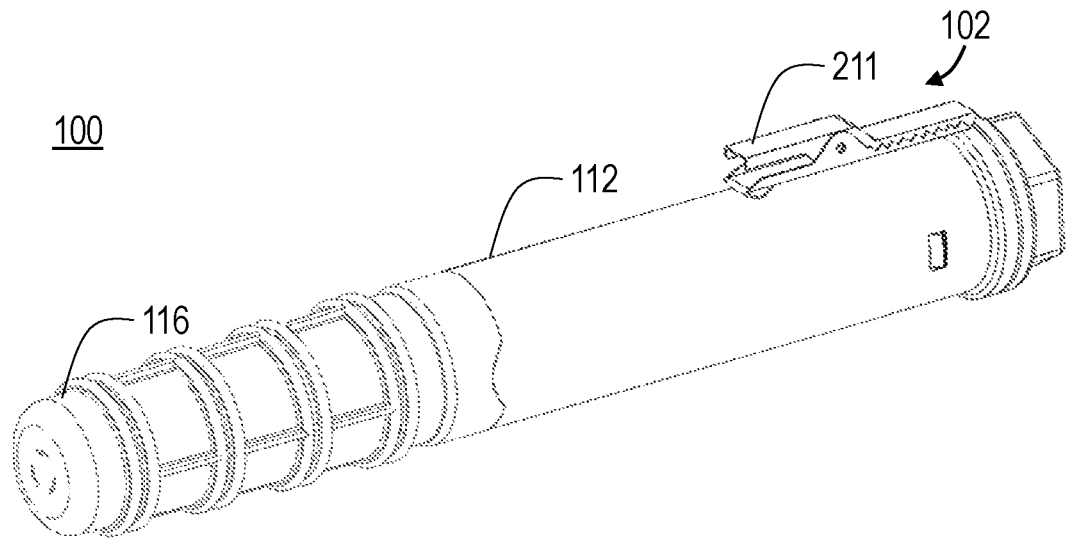
FIG. 38 is a perspective view of an alternative embodiment of the plunger of the injector of FIG. 1.
Figure 39:
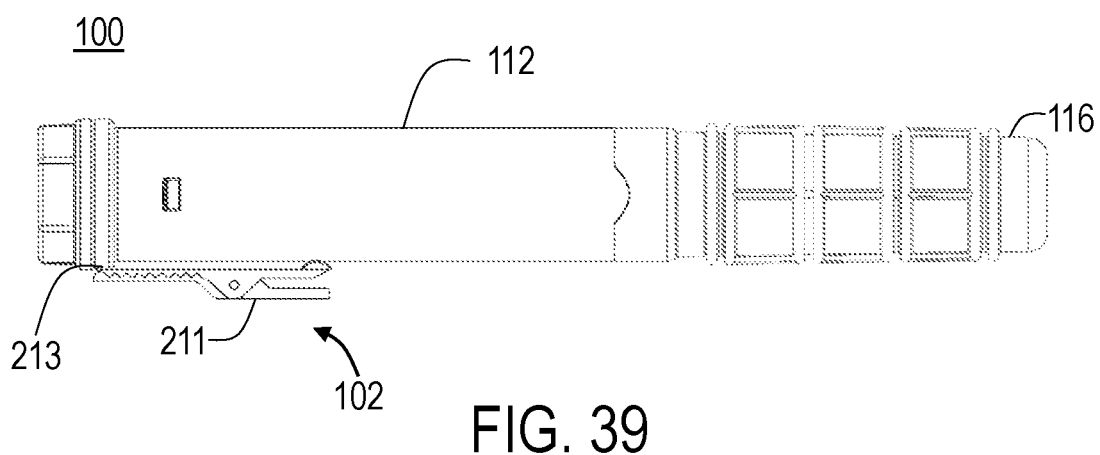
FIG. 39 is a side view of the plunger of the injector of FIG. 38.

FIG. 20 shows a perspective view of the plunger 102. The plunger 102 includes a cap portion 202 and a plunger rod 204 extending from the cap portion 202. The plunger rod 204 can include a threaded portion 205 at the end opposite the cap portion 202 for engaging the plunger seal 200 of the syringe 106. During assembly of the injector 100, the plunger rod 204 is inserted through aperture 130 in the cam 108 and through the aperture 158 in the inner sleeve 110 so that the plunger rod 204 can engage the plunger seal 200 of the syringe 106. The plunger 102 can further include one or more arms 206 extending from the cap portion 202 for engaging the apertures 178 in the outer sleeve 112 to lock the plunger 102 to the outer sleeve 112, as shown in FIG. 2, for example. Each arm 206 can include an outwardly extending tooth 208 for engaging the aperture 178. During assembly, each tooth 208 contacts a respective one of the ramps 180 on the outer sleeve 112 and the arm 206 flexes radially inward. When the tooth 208 reaches the aperture 178 the arm 206 flexes back toward its natural position such that the tooth 208 engages the aperture 178. With the teeth 208 engaged with the apertures 178, the plunger 102 is locked to the outer sleeve 112 such that they translate together during use, as described herein. As illustrated, for example, in FIGS. 20 and 21, the plunger 102 can further include a clip 210 extending from the cap portion 202 that can be used to clip the injector 100 to a belt or other item for ease of transportation and retrieval of the injector 100. In another example, as illustrated in FIGS. 38 and 39, the plunger 102 can alternatively include an alligator clip 211 that can be used to clip the injector 100 to a belt or other item for ease of transportation and retrieval of the injector 100. In some cases, the alligator clip 211 may be molded into a portion of the injector 100. For example, an end 213 of the alligator clip 211 may be molded into the outer sleeve 112 of the injector, thereby securing the alligator clip 211 to the injector 100. In some other cases, the alligator clip 211 may be removably coupled to the injector 100. For example, the end 213 of the alligator clip 211 may include a ring-like structure that when placed on the outer sleeve 112 expands over the outer sleeve 112 and snaps around the surface of the outer sleeve 112 to fasten to the injector 100. In such cases, the alligator clip 211 may be a separate component from the plunger 102.

Figure 21:
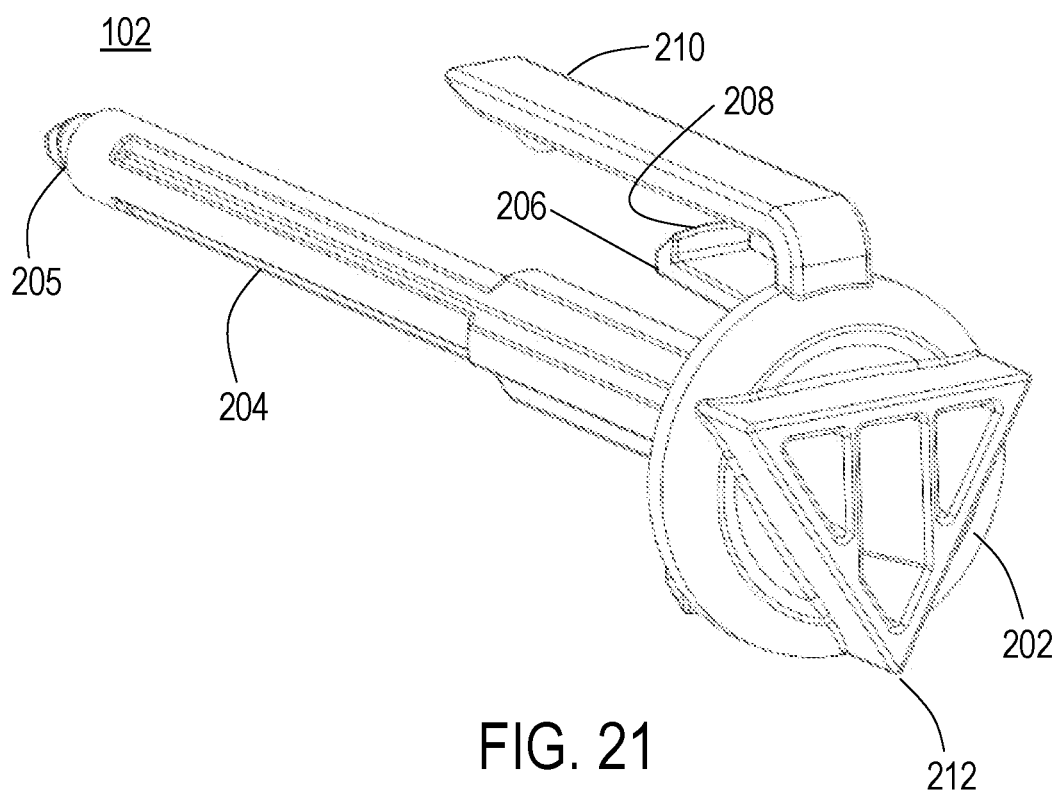
FIG. 21 is a perspective view of an alternative embodiment of the plunger of the injector of FIG. 1.
Figure 22:
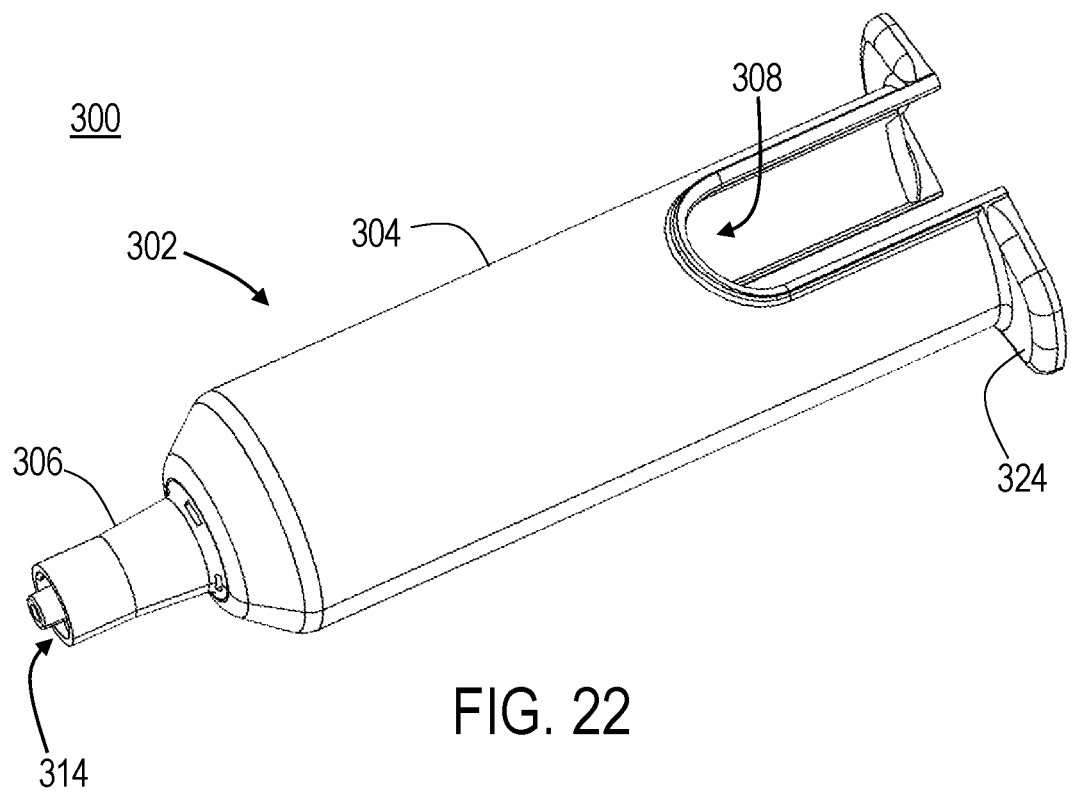
FIG. 22 is a perspective view of a Luer adapter configured for use with the injector of FIG. 1, according to one embodiment described herein.
Figure 23:
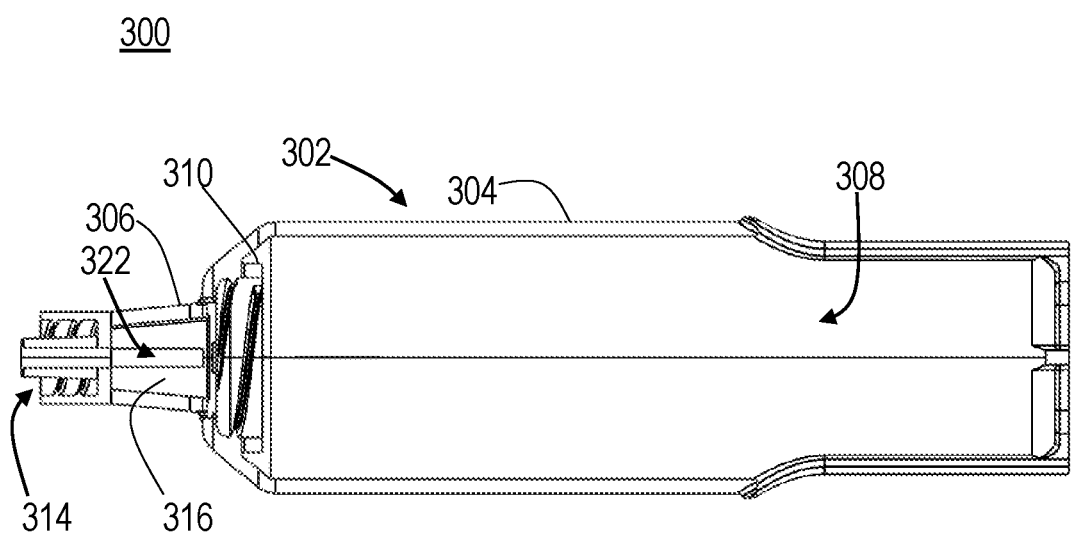
FIG. 23 is a side cross-sectional view of the Luer adapter of FIG. 22.
Figure 24:
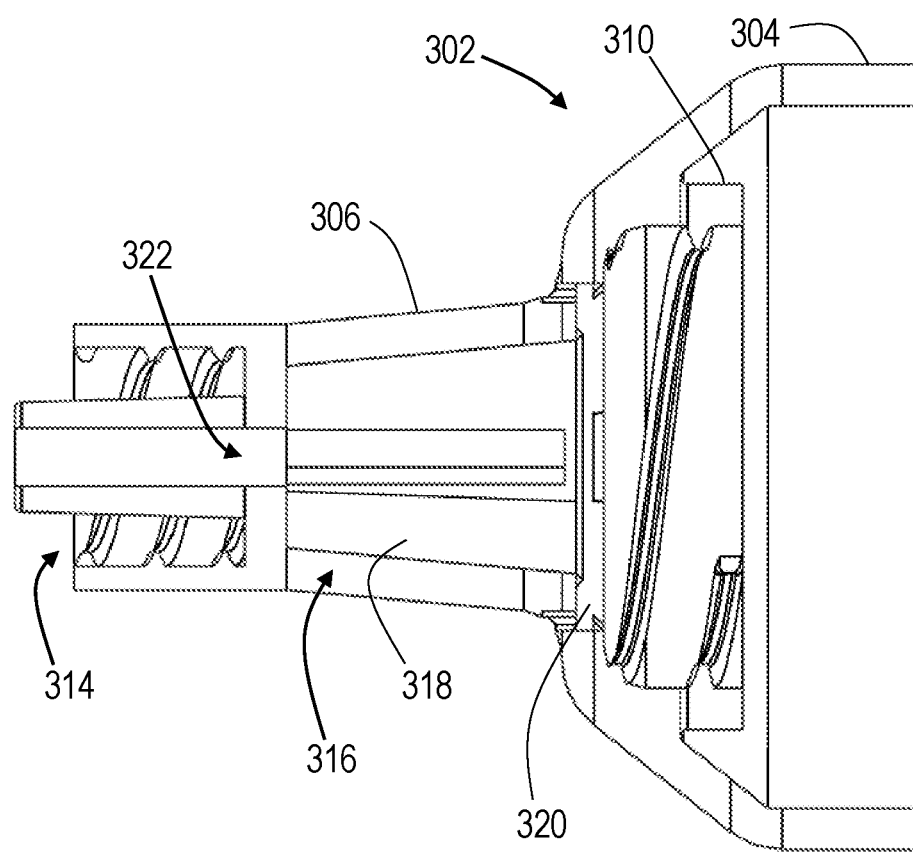
FIG. 24 is a detail side cross sectional view of the tip of the Luer adapter of FIG. 22.

In some embodiments, as shown in FIG. 21, the cap 116 of the plunger 102 includes an indicator 212 that corresponds to the type of medicament contained in the syringe 106. For example, the indicator 212 can be in the shape of a circle, an oval, a hexagon, a trapezoid, a heart, a star, or any other appropriate or desired shape.

The biasing member 104 can be, for example, a helical coil spring. However, it should be understood that the biasing member 104 can take on other forms. For example, the biasing member 104 can be a compressible, elastomeric component.

The operation of the injector 100 will now be described. FIGS. 1 and 2 show side and side cross-sectional views, respectively, of the injector 100 in an initial configuration, which may be the configuration in which the injector 100 is provided to users. In this initial configuration, the cap 116 is in place on the injector 100 and is coupled to the outer sleeve 112. Specifically, the ramped projections 176 on the outer sleeve 112 are disposed in the recesses 184 on the cap 116 and the bead 182 on the cap 116 is disposed in the groove 174 in the outer sleeve 112. In addition, the teeth 190 of the needle cover engagement member 114 are engaged with the needle cover 198 of the syringe 106. When the user is ready to use the injector 100, the user can twist and/or pull the cap 116 with respect to the outer sleeve 112 to remove the cap 116 from the injector 100. Removal of the cap 116 also removes the needle cover 198 due to the engagement of the teeth 190 with the needle cover 198.

Figure 12A:
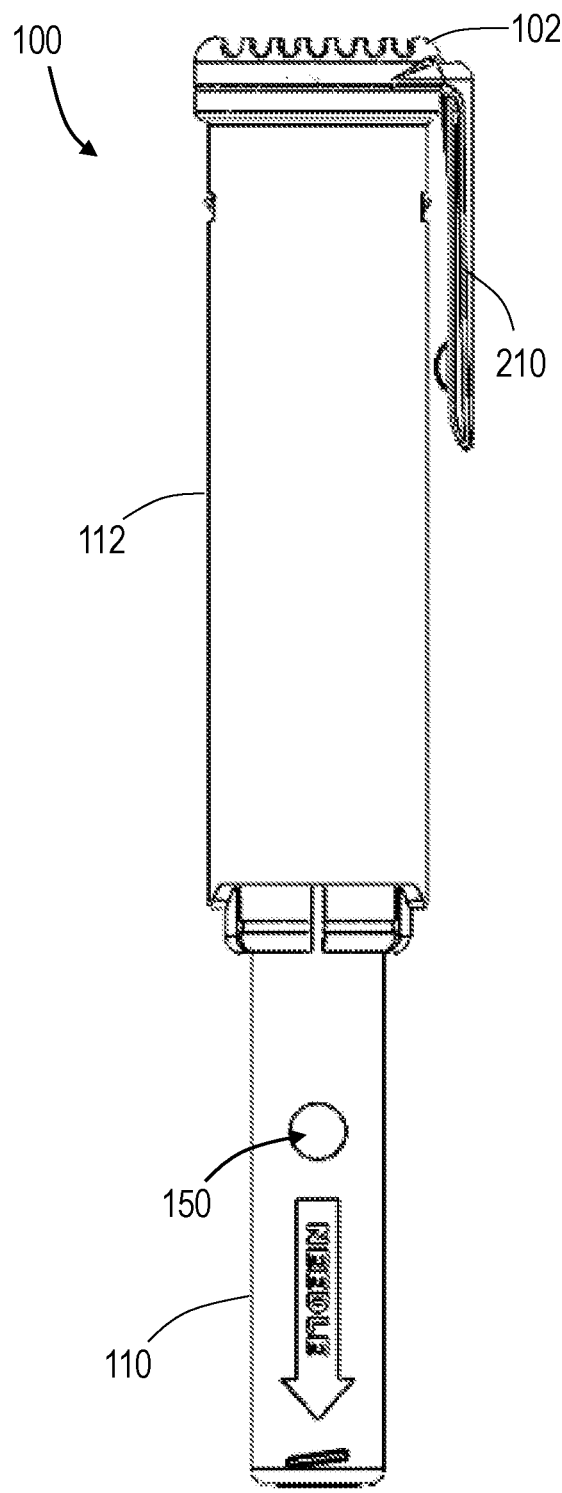
FIGS. 12A and 12B are side and side cross-sectional views, respectively, of the injector of FIG. 1 after removal of the cap.
Figure 12B:
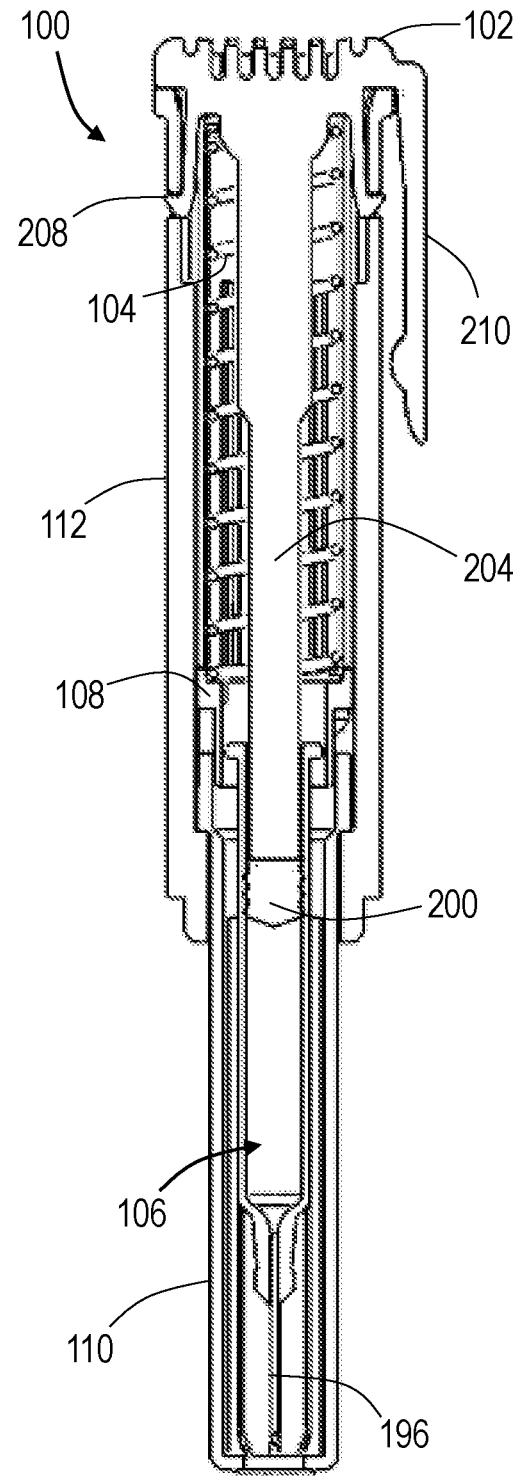

FIGS. 12A and 12B show side and side cross-sectional views, respectively, of the injector 100 after removal of the cap 116. As can be seen in these figures, the inner sleeve 110 is extended, as a result of the force applied by the biasing member 104, such that the inner sleeve 110 shields the needle 196 of the syringe 106. As shown in FIG. 12B, the biasing member 104 is positioned such that one end of the biasing member 104 is in contact with the cap portion 202 of the plunger 102 and the opposite end of the biasing member 104 is in contact with the cam 108. With the injector 100 in the configuration shown in FIGS. 12A and 12B, the biasing member 104 may be fully extended or nearly fully extended. As a result, the biasing member 104 is not imparting a large force on the inner sleeve 110 or the other components of the injector 100. This allows the injector 100 to be stored for long durations without fear that components will be damaged or become permanently deformed as a result of being exposed to high forces during storage. This may provide an advantage over prior art devices that include springs or other biasing members that are in a compressed or loaded state during storage. The ring 140 of the inner sleeve 110 is in contact with the shoulder 170 of the outer sleeve 112 to prevent the inner sleeve 110 from falling out of the outer sleeve 112.

Figure 16A:
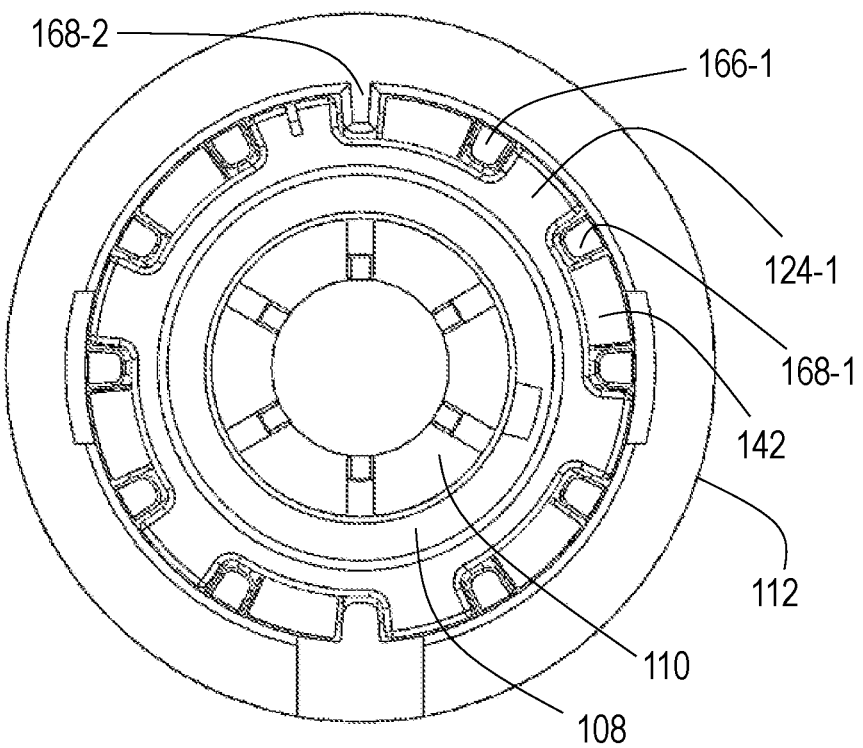
FIG. 16A is an end view of the outer sleeve, inner sleeve, and cam of the injector of FIG. 1 prior to injection of medicament.
Figure 17A:
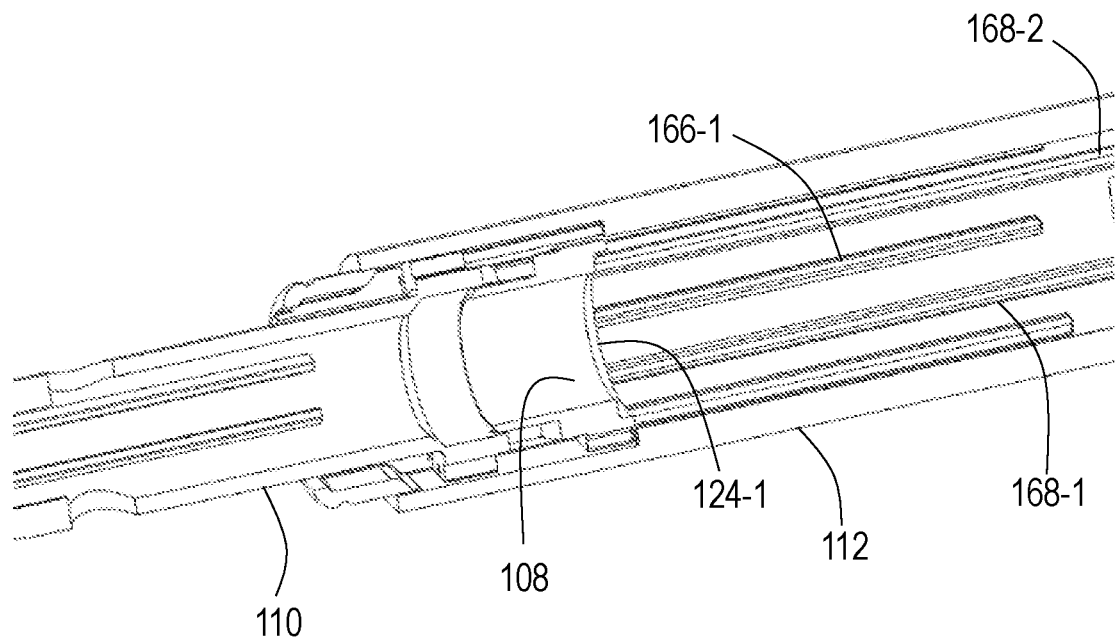
FIG. 17A is a cross-sectional perspective view of the outer sleeve, inner sleeve, and cam of the injector of FIG. 1 prior to injection of medicament.
Figure 34:
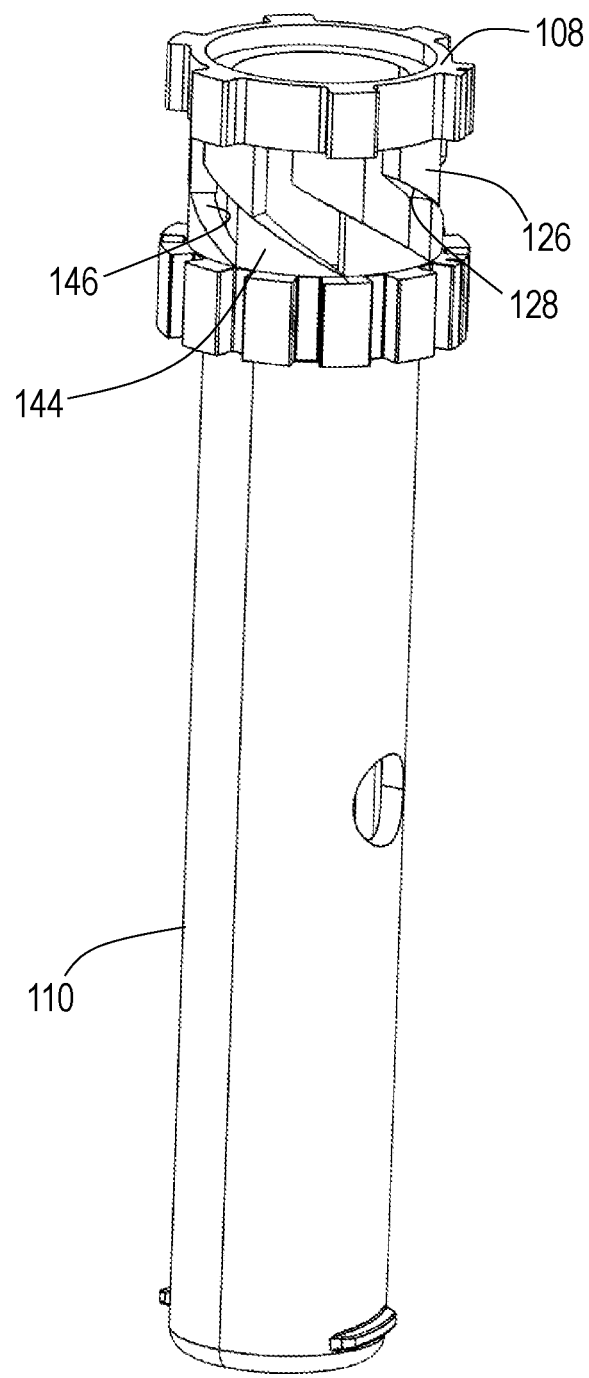
FIG. 34 is a perspective view of cam and the inner sleeve of the injector of FIG. 1 showing the engagement of the cam elements of the cam with the cam teeth of the inner sleeve.

FIG. 16A shows an end view of the outer sleeve 112, the inner sleeve 110, and the cam 108 when the injector 100 is in the configuration shown in FIGS. 12A and 12B, and FIG. 17A shows a cross-sectional perspective view of the same components in this configuration, at a first operational stage. The other components of the injector 100 are not shown for illustrative purposes. As shown in FIG. 34, the cam teeth 144 of the inner sleeve 110 are in contact with the cam elements 126 of the cam 108. Any appropriate number of cam teeth 144 and cam elements 126 can be used. For example, in one embodiment, the inner sleeve 110 includes seven cam teeth 144 (as shown in, for example, FIG. 7) and the cam 108 includes seven cam elements 126 (as shown in, for example, FIG. 5A). In another example, in another embodiment, the inner sleeve 110 includes six cam teeth 144 (as shown in, for example, FIG. 37) and the cam 108 includes six cam elements 126 that correspond to the six cam teeth 144. The angle that the interfacing surfaces (cam faces 128 and angled faces 146) make with the longitudinal axis A can be chosen to provide the desired circumferential force on the cam 108. For example, in one embodiment, these interfacing surfaces each define a helix angle of about 30 degrees with respect to the longitudinal axis A.

Figure 33:
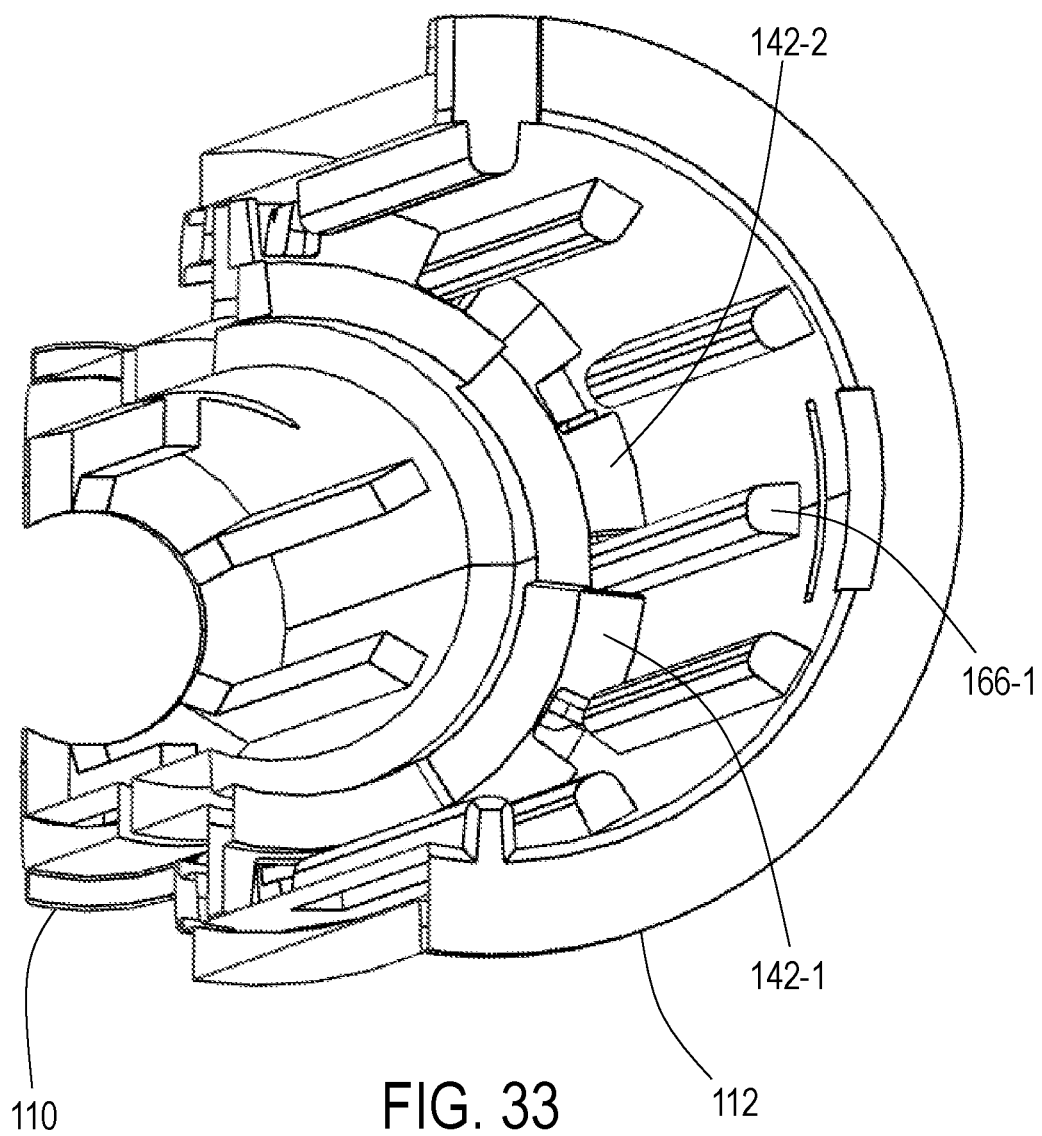
FIG. 33 is a cross-sectional perspective view of the outer sleeve and the inner sleeve of the adapter of FIG. 1.

As shown in FIG. 33, the projections 142 of the inner sleeve 110 are disposed on opposite sides of respective first ribs 166 of the outer sleeve 112, with this engagement preventing rotation of the inner sleeve 110 with respect to the outer sleeve 112 during use of the injector 100. For example, projections 142-1 and 142-2 are positioned on opposite sides of first rib 166-1. Each protrusion 124 of the cam 108 is positioned between a first rib 166 and a second rib 168 of the outer sleeve 112. For example, as shown in FIGS. 16A and 17A, the protrusion 124-1 is positioned between first rib 166-1 and second rib 168-1. The inner sleeve 110 can include more projections 142 than the cam 108 has protrusions 124. As a result, the inner sleeve 110 can include a projection 142 on each side of each first rib 166 while the cam 108 has a protrusion 124 on only a single side of each first rib 166.

When the user wishes to inject the medicament contained in the syringe 106, the user brings the second end 138 of the inner sleeve 110 into contact with the injection site (i.e., the patient's tissue). With the inner sleeve 110 in contact with the injection site, applying pressure on the plunger 102 causes the outer sleeve 112 to translate toward the injection site and over the inner sleeve 110, thereby compressing the biasing member 104. As the outer sleeve 112 travels forward, the projections 142 of the inner sleeve 110 and the protrusions 124 of the cam 108 engage and slide along the first ribs 166 and the second ribs 168.

Figure 14A:
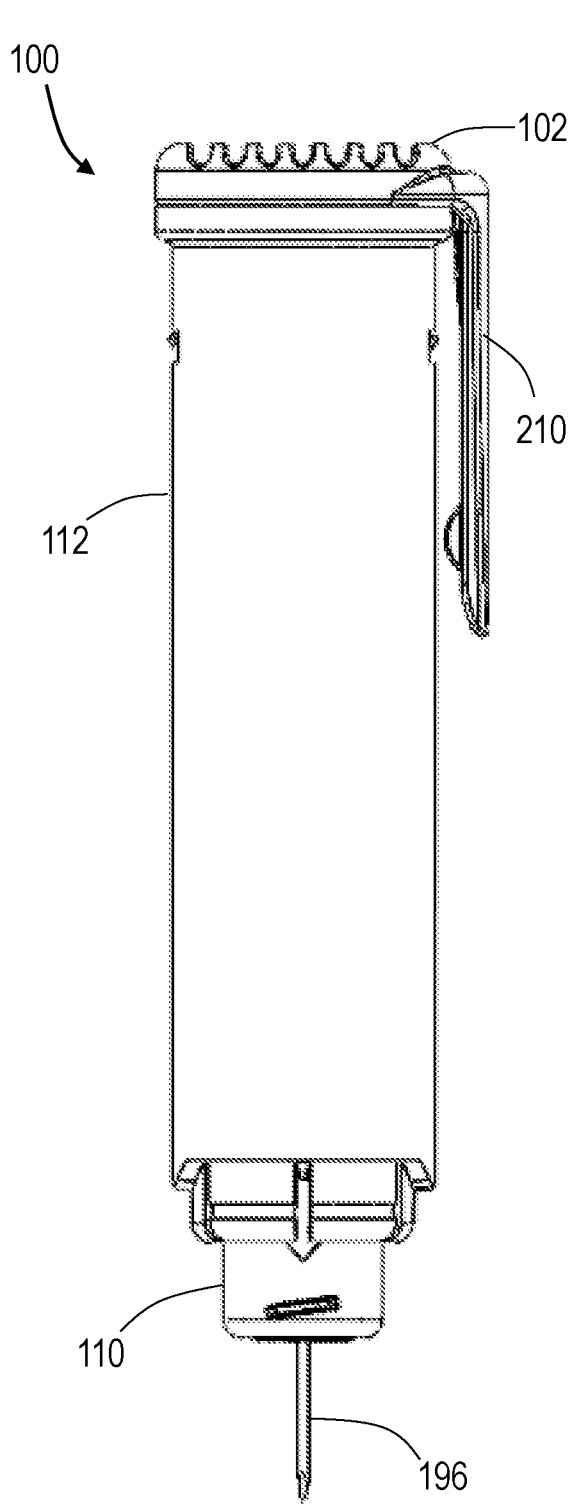
FIGS. 14A and 14B are side and side cross-sectional views, respectively, of the injector of FIG. 1 after delivery of the medicament.
Figure 14B:
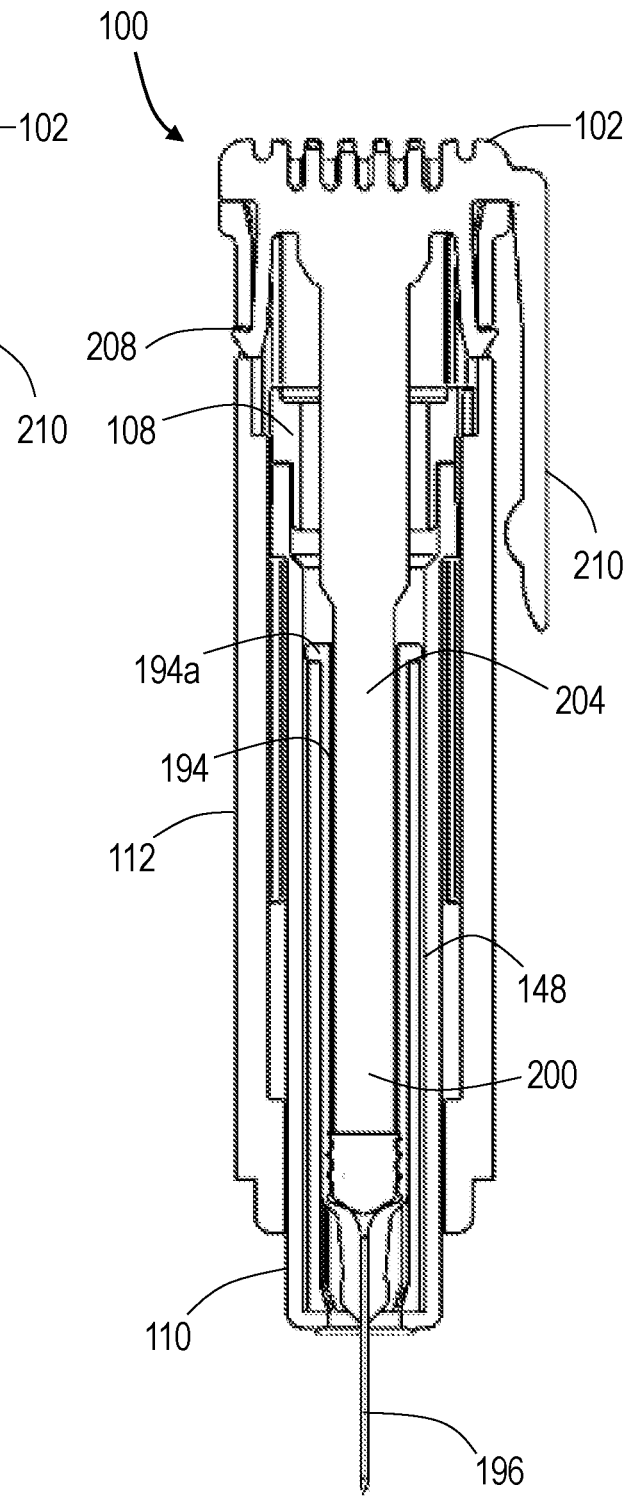

As the plunger 102 and the outer sleeve 112 translate forward, the syringe 106 is also moved forward as a result of the pressure applied by the plunger 102 on the plunger seal 200. The forward movement of the syringe 106 causes the needle 196 to extend through the aperture 158 at the end of the inner sleeve 110, as shown in FIGS. 13A and 13B, and be inserted into the injection site (i.e., the patient's tissue). The biasing member 104 is not shown in FIGS. 13 and 14 for clarity, but it should be understood that the biasing member 104 would be present and compressed in these configurations. The syringe 106 moves forward until the flange 194a at the end of the barrel 194 contacts the end of the ribs 148 in the inner sleeve 110. With the flange 194a in contact with the ribs 148, further translation of the syringe barrel 194 with respect to the inner sleeve 110 is prevented and continued depression of the plunger 102 causes translation of the plunger seal 200 within the barrel 194 and injection of the medicament stored within the barrel 194. This position is shown in FIGS. 14A and 14B. The length of the ribs 148 (i.e., the distance from the end of the ribs 148 to the front face of the inner sleeve 110) can be chosen to provide the desired insertion depth of the needle 196. Because the contact of the flange 194a of the syringe barrel 194 with the ribs 148 controls the extent of the needle 196 that extends from the inner sleeve 110, changing the length of the ribs 148 may change the depth of insertion. Changing the length of the ribs 148 may also be used to customize the injector 100 for use with different syringes 106 or needles 196. This controlled depth of insertion provides advantages in controlling the depth of insertion to ensure the medicament is injected in the proper location (e.g., intramuscular injections).

Figure 16B:
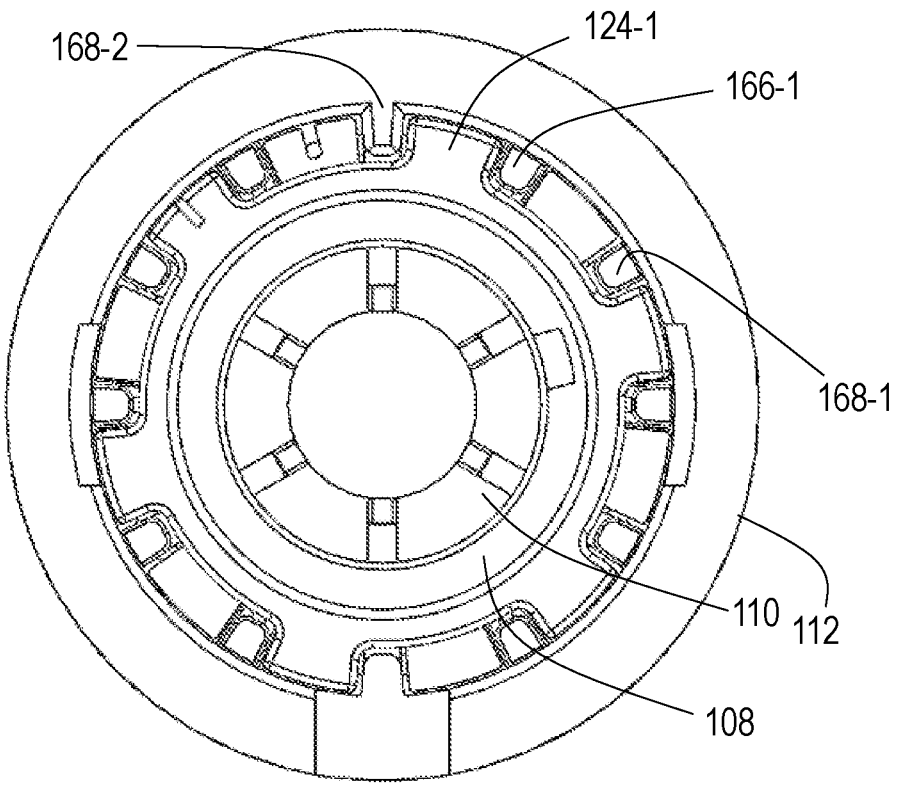
FIG. 16B is an end view of the outer sleeve, inner sleeve, and cam of the injector of FIG. 1 after completion of injection of the medicament.
Figure 17B:
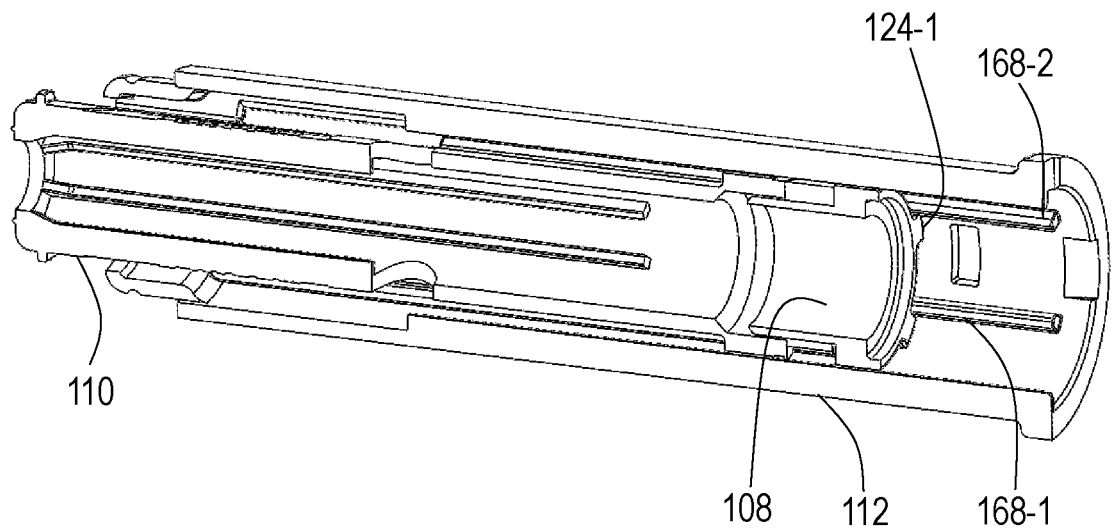
FIG. 17B is a cross-sectional perspective view of the outer sleeve, inner sleeve, and cam of the injector of FIG. 1 after completion of injection of the medicament.

When the end of the injection is reached (i.e., when the desired amount of medicament in the syringe 106 has been injected), the protrusions 124 of the cam 108 reach the end of the first ribs 166. Once the protrusions 124 clear the first ribs 166, the contact of the cam faces 128 of the cam elements 126 and the angled faces 146 of the projections 142 on the inner sleeve 110 causes the cam 108 to rotate. As can be seen by comparing the position of protrusion 124-1 in FIGS. 16A and 16B and in FIGS. 17A and 17B, the cam 108 has rotated counterclockwise. Rotation of the cam 108 causes each protrusion 124 to contact a respective one of the second ribs 168 (e.g., protrusion 124-1 contacts second rib 168-2). This contact can provide audible (e.g., a "click") and/or tactile feedback to the user that injection is complete (e.g., a clicking sound). The length of the first ribs 166 can be chosen to achieve the desired stroke of the plunger rod 205—and, thereby, the plunger seal 200—within the syringe barrel 194. This ensures the proper amount of medicament is delivered prior to the audible or tactile indication that delivery is complete. The length of the first ribs 166 can be customized based on the length of the syringe barrel 194. This may allow the injector 100 to be configured for different syringe sizes without modifying each of the components of the injector 100. For example, the plunger 102, the cam 108, the inner sleeve 110, and the cap 116 can be used with an outer sleeve 112 that has first ribs 166 customized to fit a particular syringe. This may reduce tooling costs and simplify and reduce the amount of inventory that a manufacturer must carry.

Figure 15A:
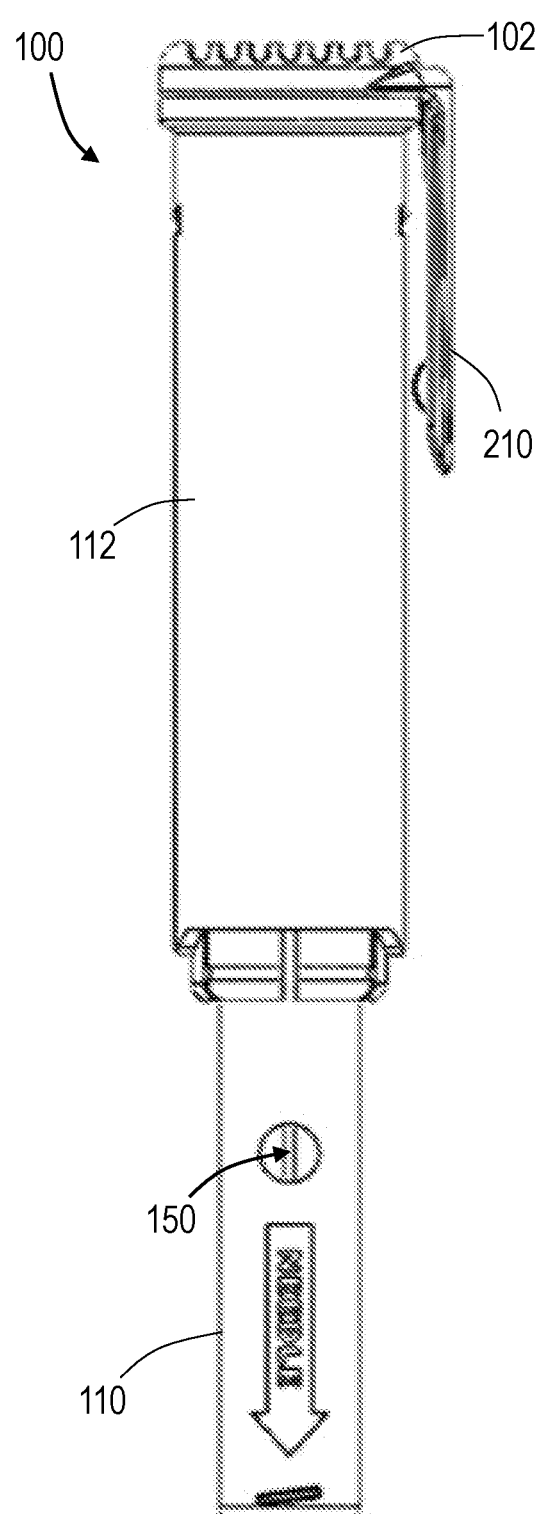
FIGS. 15A and 15B are side and side cross-sectional views, respectively, of the injector of FIG. 1 after the inner sleeve extends over the needle of the syringe.
Figure 15B:
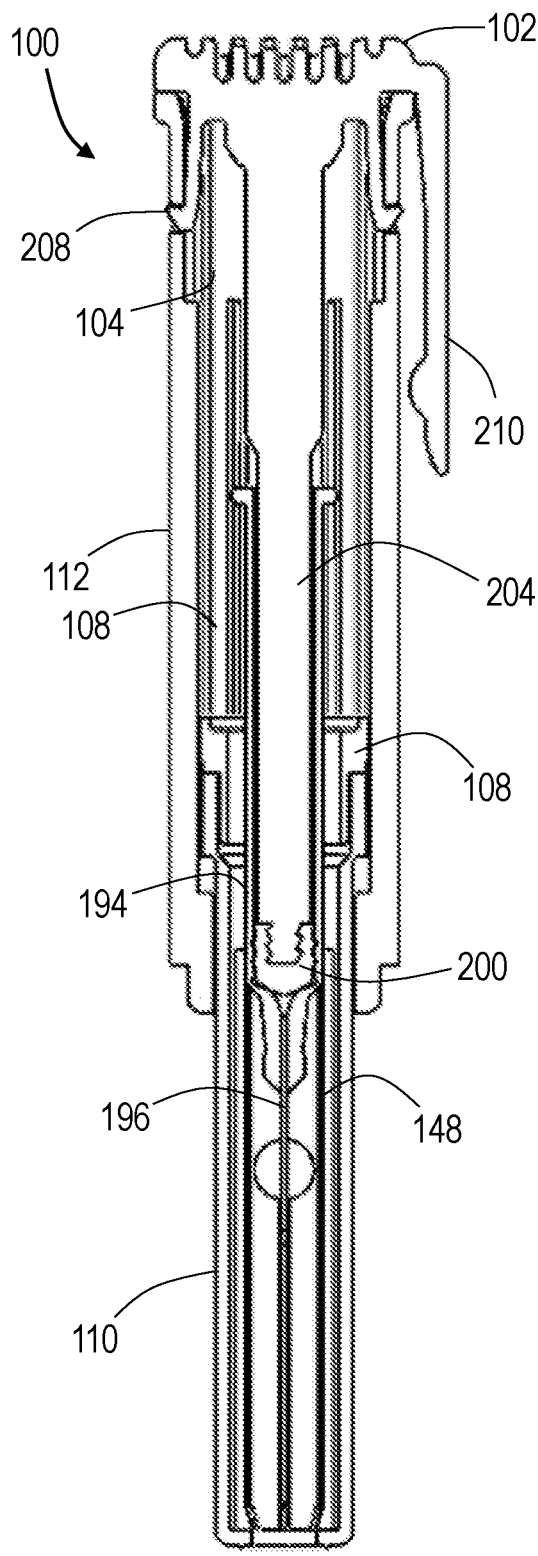
Figure 16C:
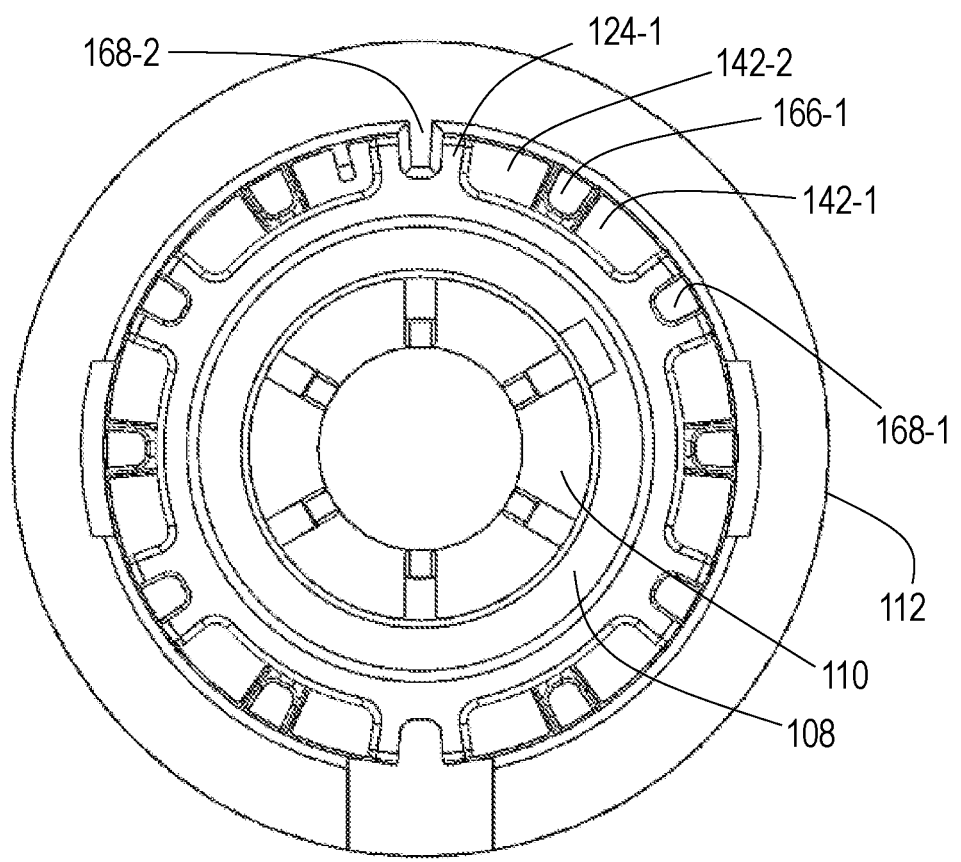
FIG. 16C is an end view of the outer sleeve, inner sleeve, and cam of the injector of FIG. 1 after extension and lockout of the inner sleeve.
Figure 17C:
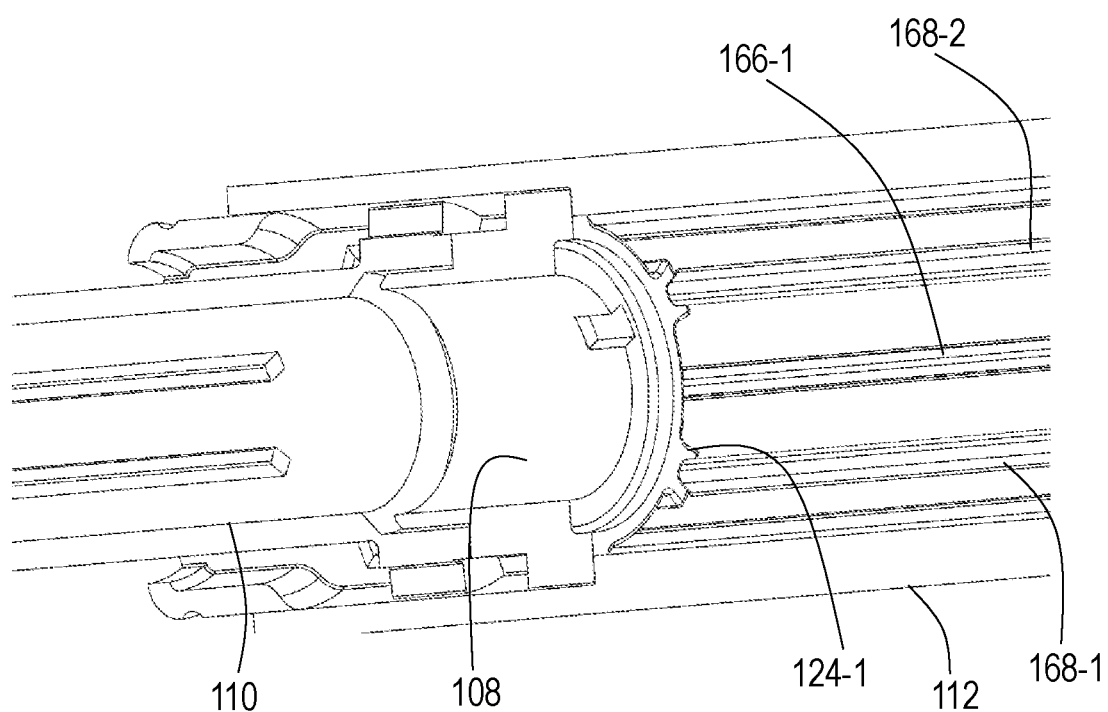
FIG. 17C is a cross-sectional perspective view of the outer sleeve, inner sleeve, and cam of the injector of FIG. 1 after extension and lockout of the inner sleeve.

After completion of the injection, the user can begin to remove the injector 100 from the injection site. As the user does so, the inner sleeve 110 and cam 108, under the urging of the biasing member 104, travel back toward the second end 164 of the outer sleeve 112 to the position shown in FIGS. 15A and 15B. When the protrusions 124 of the cam 108 reach the end of the second ribs 168, the contact of the cam faces 128 of the cam elements 126 and the angled faces 146 of the cam teeth 144 again causes rotation of the cam 108. In this case, the cam 108 rotates such that the cam elements 126 move toward, and may come in contact with, the vertical faces 147 (shown in FIG. 7) of the cam teeth 144. When the cam 108 comes to a stop, each protrusion 124 of the cam 108 is aligned and engaged in contact with the end of a respective one of the second ribs 168. For example, as shown in FIGS. 16C and 17C, protrusion 124-1 is aligned with and in contact with the end of second rib 168-2. In this position, at a second operational stage, the cam 108 and inner sleeve 110 cannot translate axially within the outer sleeve 112. Thus, the inner sleeve 110 and the outer sleeve 112 are locked in their positions. As a result, the inner sleeve 110 cannot be retracted and the needle 196 cannot again be exposed from the end of the inner sleeve 110. This prevents inadvertent needle stick injuries that can occur with prior art injectors.

In another aspect, as shown in FIGS. 22-26, a Luer adapter 300 to be used with the injector 100 is provided. The Luer adapter 300 allows the medicament in the syringe 106 to be provided to a patient via, for example, an intravenous line. The Luer adapter 300 includes a body 302 having a cylindrical portion 304 and a tip 306 at one end of the cylindrical portion 304. The cylindrical portion 304 defines a cavity 308 that is open at the end of the cylindrical body 302 that is opposite the tip 306. The cavity 308 is configured to at least partially receive the injector 100. The adapter 300 includes an interior wall 310 defining threads to engage the ridges 152 at the end of the inner sleeve 110 to couple the adapter 300 to the inner sleeve—for example, by way of a ¼ turn thread engagement.

At the end of the tip 306, the adapter 300 includes a Luer connector 314. The Luer connector 314 can be a male Luer connector for connection to a female Luer fitment of a tubing set. Alternatively, the Luer connector 314 can be a female Luer connector for connection to a male Luer fitment. The connection of the adapter 300 with the tubing set may, for example, use locking or slipping type Luer connections, such as those sold under the names LUER-LOK™ and LUER-SLIP™ by Becton Dickinson.

The adapter further includes a diaphragm 316 positioned within the tip 306. The diaphragm 316 includes a frustoconical portion 318 and a flange 320. The flange 320 is configured to be positioned between a shoulder of the adapter 300 and the inner sleeve 110. The diaphragm 316 can be sealed by ribs on the inner sleeve (e.g., rib 154) and the shoulder of the adapter 300. During use, the frustoconical portion 318 of the diaphragm 316 is pierced by the needle 196 of the syringe 106. The diaphragm 316 can be constructed from, for example, an elastomeric material. The diaphragm 316 is configured to ensure that the medicament is delivered though the Luer connector 314 and does not leak from the injector 100 or the Luer adapter 300.

Figure 26:
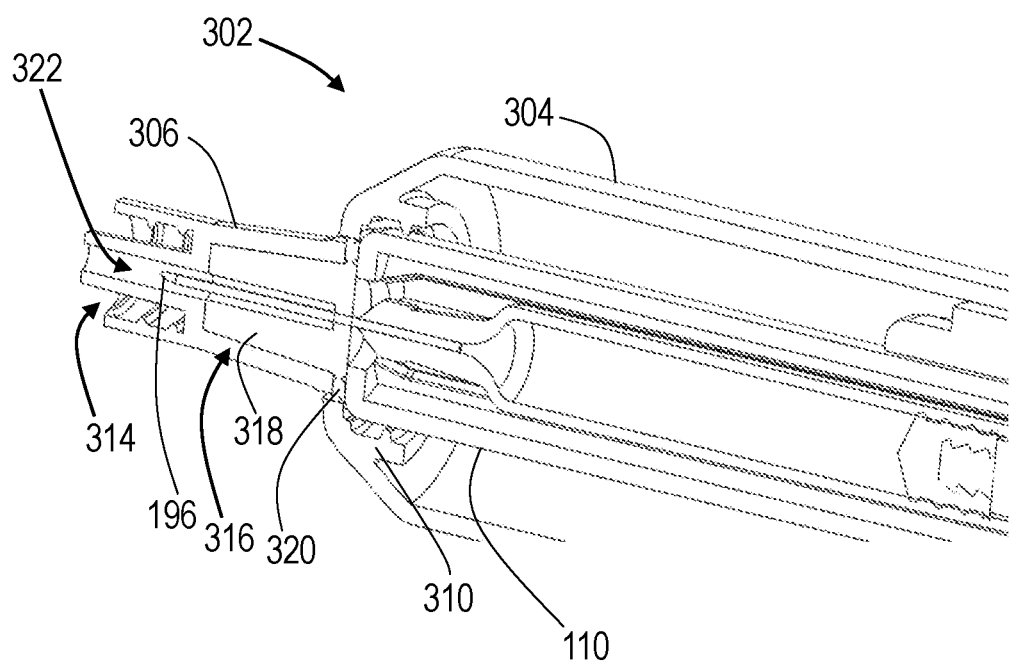
FIG. 26 is a detail cross-sectional perspective view of the Luer adapter of FIG. 22 attached to the adapter of FIG. 1 after extension of the needle of the syringe.
Figure 27:
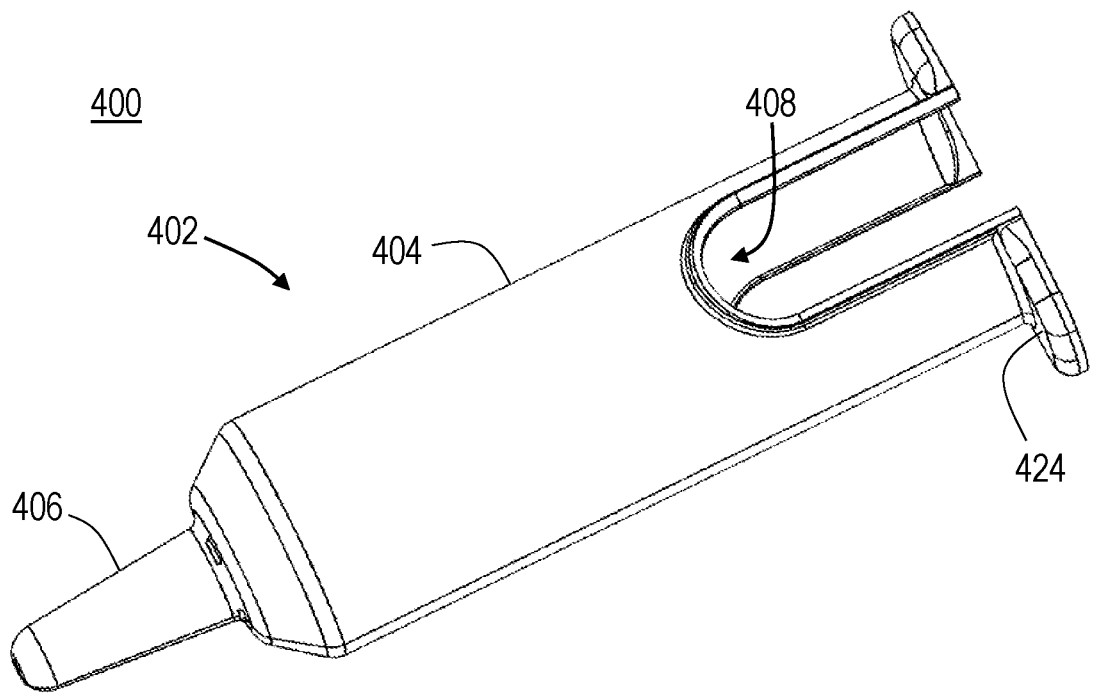
FIG. 27 is a perspective view of a nasal spray adapter configured for use with the injector of FIG. 1, according to one embodiment described herein.

The connector 314 and the diaphragm 316 together define a channel 322 within which the needle 196 is at least partially disposed while the medicament is injected, as shown in FIG. 26.

The adapter 300 can further include finger flanges 324 extending outward from the cylindrical portion 304. To deliver the medicament from the syringe 106, the user can grasp the injector 100 with the user's fingers around the finger flanges 324 and with the cap portion 202 of the plunger 102 resting against the user's palm. The user can then squeeze to cause dispensing of the medicament. After dispensing the medicament, the user can release to allow the inner sleeve 110 to slide outward with respect to the inner sleeve 110, as described above, such that the needle 196 is retracted from the diaphragm 316. With the position of the inner sleeve 110 locked, the user can then remove the adapter 300 from the injector 100 and dispose of both the injector 100 and the Luer adapter 300.

Figure 25:
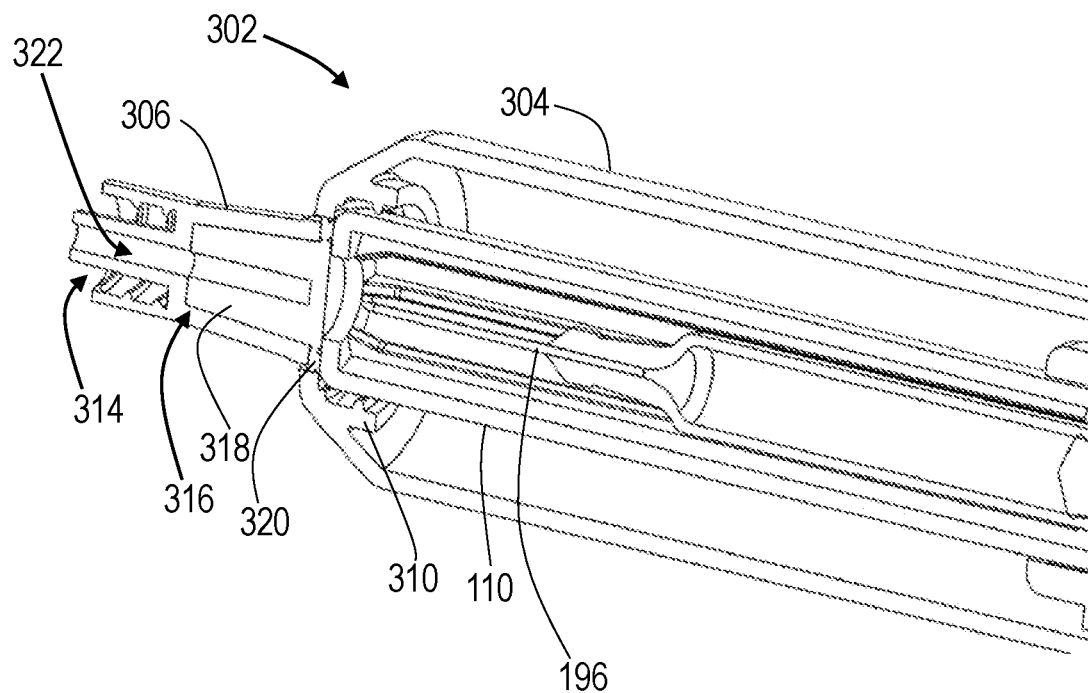
FIG. 25 is a detail cross-sectional perspective view of the Luer adapter of FIG. 22 attached to the injector of FIG. 1.

FIG. 25 shows the adapter 300 coupled to the injector 100. As shown, the second end 138 of the inner sleeve 110 is engaged with the diaphragm 316 and the needle 196 is disposed in the inner sleeve 110. FIG. 26 shows the injector 100 and the adapter 300 after depression of the plunger 102 and the outer sleeve 112 to extend the needle 196 and pierce the frustoconical portion 318 of the diaphragm 316 such that it is disposed in the channel 322. With the needle 196 in this position, depression of the plunger 102 causes the medicament to be dispensed through tubing coupled to the Luer connector 314.

In another embodiment, a nasal spray adapter 400 is provided for use with the injector 100. The nasal spray adapter 400 allows the medicament in the syringe 106 to be provided to a patient via nasal delivery. The nasal spray adapter 400 includes a body 402 having a cylindrical portion 404 and a tip 406 at one end of the cylindrical portion 404. The cylindrical portion 404 defines a cavity 408 configured to partially receive the injector 100. The adapter 400 includes an interior wall 410 defining threads to engage the ridges 152 at the end of the inner sleeve 110 to couple the adapter 400 to the inner sleeve—for example, by way of a ¼ turn thread engagement.

Figure 30:
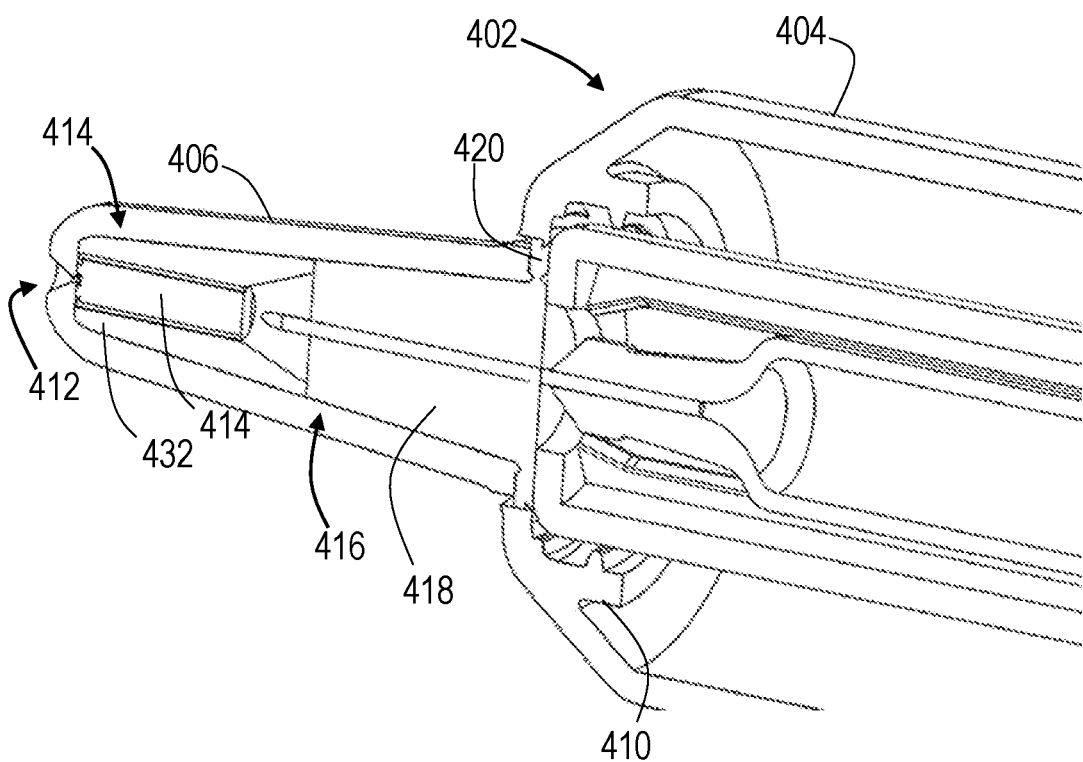
FIG. 30 is a detail side cross-sectional view of the nasal spray adapter of FIG. 27 attached to the injector of FIG. 1.

At the end of the tip 406, the adapter 400 includes an aperture 412 to allow medicament to be expelled into a user's nasal passages via a spray. The adapter 400 further includes a diaphragm 416 positioned within the tip 406. The diaphragm 416 includes a frustoconical portion 418 and a flange 420. The flange 420 is configured to be positioned between a shoulder of the adapter 400 and the second end 138 of the inner sleeve 110. The diaphragm 416 can be sealed by ribs on the inner sleeve 110 (e.g., rib 154) and the adapter 400. During use, the frustoconical portion 418 of the diaphragm 416 is pierced by the needle 196 of the syringe 106, as shown in FIG. 30, so that the medicament can be expelled through the aperture 412. The diaphragm 416 can be constructed from, for example, an elastomeric material. The diaphragm 416 is configured to ensure that the medicament is delivered though the aperture 412 and does not leak from the injector 100 or the adapter 400.

Figure 28:
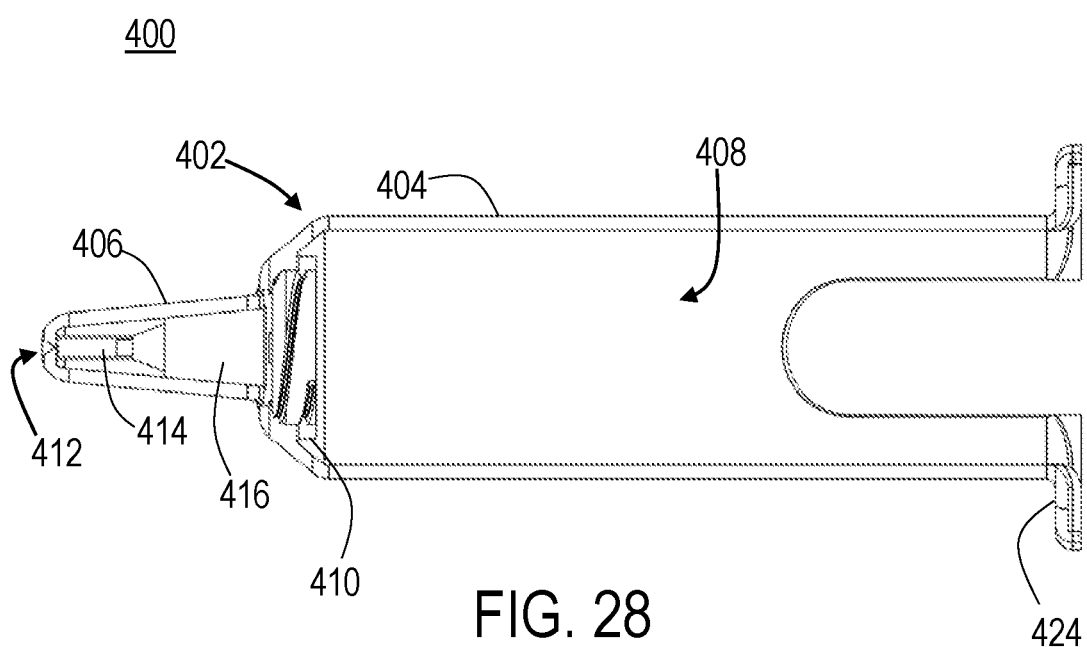
FIG. 28 is a side cross-sectional view of the nasal spray adapter of FIG. 27.
Figure 29:
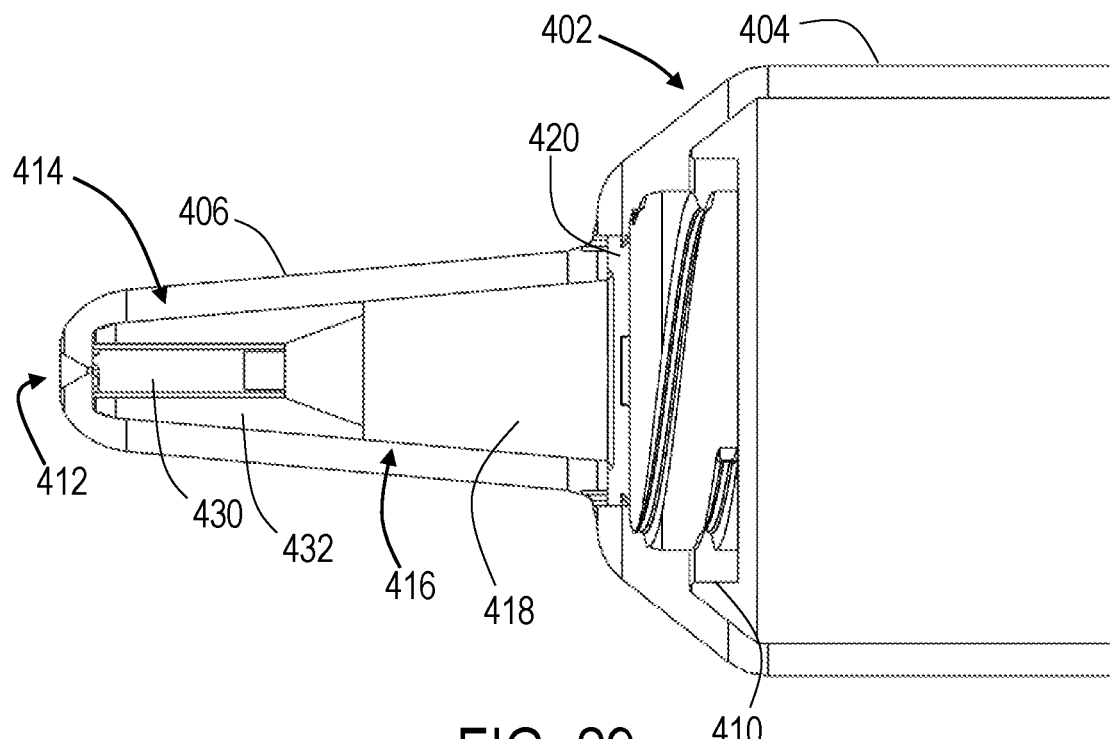
FIG. 29 is a detail side cross sectional view of the tip of the nasal spray adapter of FIG. 27.
Figure 35:
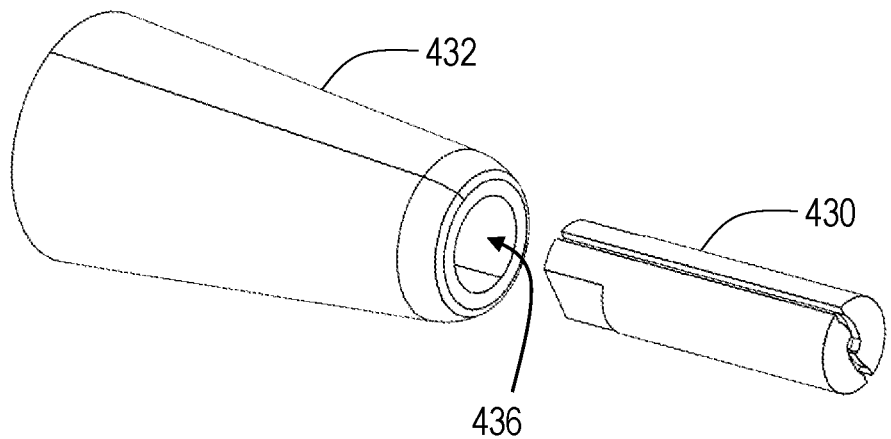
FIG. 35 is an exploded view of an atomizing insert of the nasal spray adapter of FIG. 27.
Figure 36:
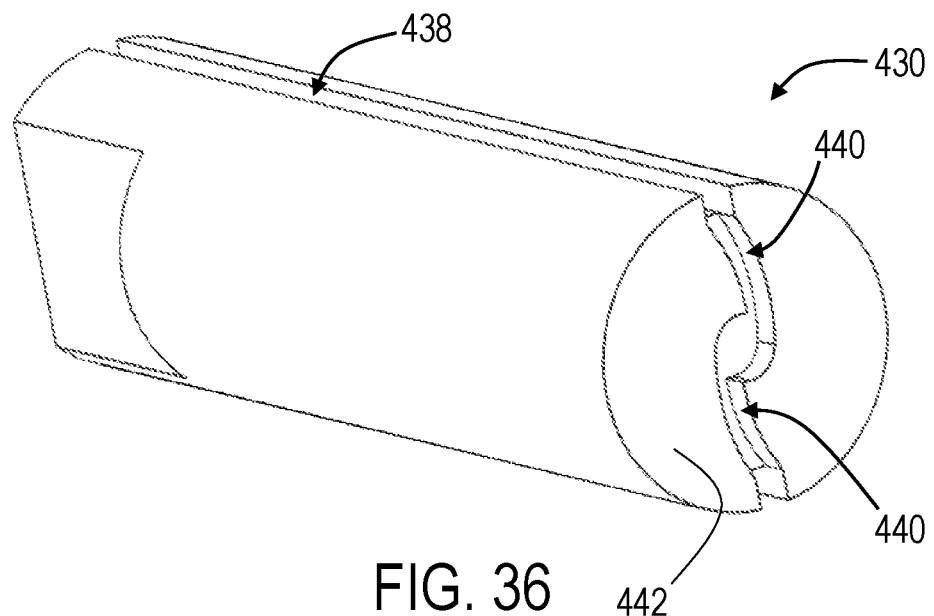
FIG. 36 is a perspective view of the inner member of the atomizing insert of FIG. 35.

Further, as shown in FIG. 28 an atomizing insert 414 can be positioned in the tip 406 adjacent to the aperture 412. The atomizing insert 414 may convert the medicament into fine particles or droplets for delivery to the patient via the aperture 412. The atomizing insert 414 is shown in more detail in the cross-sectional views of FIGS. 29 and 30 and in FIGS. 35 and 36. As shown in FIGS. 29 and 30, the atomizing insert 414 is positioned in the tip 406 between the diaphragm 416 and the aperture 412. FIG. 36 shows an exploded view of the atomizing insert 414. The atomizing insert 414 may include an inner member 430 and an outer member 432. The outer member 432 defines an inner passage 436 within which the inner member 430 is disposed. FIG. 36 shows a perspective view of the inner member 430. The inner member 430 may be substantially cylindrical and include one or more channels 438 extending longitudinally along the length of the inner member 430. The channels 438 allow for the flow of medicament between the inner member 430 and the outer member 432 toward the aperture 412. The inner member 430 may further include tracks 440 formed in the distal face 442 of the inner member. Each track 440 extends from a respective channel 438 toward a center of the inner member 430. The tracks 440 may meet at the center of the distal face 442 adjacent to the aperture 412. The tracks 440 may follow curved paths such that they impart a swirling motion on the medicament traveling toward the aperture 412.

The adapter 400 can further include finger flanges 424 extending outward from the cylindrical portion 404. To deliver the medicament from the syringe 106, the user can grasp the injector 100 with the user's fingers around the finger flanges 424 and with the cap portion 202 of the plunger 102 resting against the user's palm. The user can then squeeze to cause dispensing of the medicament. After dispensing the medicament, the user can release to allow the inner sleeve 110 to slide outward with respect to the inner sleeve 110, as described above, such that the needle 196 is retracted from the diaphragm 416. With the position of the inner sleeve 110 locked, the user can then remove the adapter 400 from the injector 100 and dispose of both the injector 100 and the nasal spray adapter 400.

The nasal spray adapter 400 allows for the medicament to be delivered intranasally, which avoids the need for an insertion of a needle into the patient, which may be preferable for some patients, specifically, those with a fear of needles or those with missing limbs or who lack adequate peripheral circulation. By delivering the medicament across the mucosal membrane, and to the patient's blood stream, the injector with nasal spray adapter 400 delivers an effective dose of delivery. This can be particularly useful for medicaments used to treat opioid overdoses, such as Naloxone.

In various embodiments, a kit is provided. The kit includes the injector 100, the Luer adapter 300, and the nasal spray adapter 400. By providing the nasal spray adapter 400 and the Luer adapter 300, the medicament can be delivered either via the spray nozzle to the mucosal membranes, intravenously using the Luer adapter 300, or via the needle intramuscularly, subcutaneously, intraosseously, or at any other appropriate depth. This provides the user or patient with the option at time of delivery, allowing them to choose the method of delivery which is more comfortable or most effective for them.

In another embodiment, a method of operating an injector is provided. The method includes removing a cap from the injector. The method includes placing an end of an inner sleeve against the target location. With the injector in place, a force is applied to an outer sleeve. Applying the force to the outer sleeve (i) causes axial translation of the outer sleeve and a syringe relative to the inner sleeve, (ii) causes a needle of a syringe to extend out from the distal end of the inner sleeve and into the target location, and (iii) causes the flange on the syringe barrel to contact a rib on the inner sleeve. Subsequently, a continued force is applied to the outer sleeve and plunger. Applying the continued force to the outer sleeve causes translation of a plunger rod and a seal within the syringe to cause delivery of the medicament. After delivery of the medicament, the injector is removed from the target location. A biasing member applies a force on the inner sleeve to cause the inner sleeve to translate in the distal direction with respect to the outer sleeve to cover the needle of the syringe such that the inner sleeve is locked in place with respect to the outer sleeve.

In another embodiment, a method of using an injector and a nasal spray adapter to deliver a medicament intranasally is provided. A cap of the injector is first removed. The nasal spray adapter is engaged with the injector. A tip of the nasal spray adapter is placed within or adjacent to a nostril of the patient. An outer sleeve of the injector is translated toward the tip of the nasal spray adapter to expel the medicament through the tip of the nasal spray adapter and to the patient.

In another embodiment, a method of using an injector to deliver a medicament intravenously is provided. A cap of the injector is first removed. A Luer adapter is connected to the injector. The Luer adapter is coupled to a tubing set. An outer sleeve of the injector is translated toward the Luer fitment to deliver the medicament through the Luer connector, through the tubing set, and to the patient.

While the foregoing description and drawings represent preferred or exemplary embodiments of the present invention, it will be understood that various additions, modifications and substitutions may be made therein without departing from the spirit and scope and range of equivalents of the embodiments described herein. In particular, it will be clear to those skilled in the art that the present invention may be embodied in other forms, structures, arrangements, proportions, sizes, and with other elements, materials, and components, without departing from the spirit or essential characteristics thereof. In addition, numerous variations in the methods/processes described herein may be made without departing from the spirit of the invention. One skilled in the art will further appreciate that the invention may be used with many modifications of structure, arrangement, proportions, sizes, materials, and components and otherwise, used in the practice of the invention, which are particularly adapted to specific environments and operative requirements without departing from the principles of the present invention.

What is claimed is:

1. An injector comprising:
  an outer sleeve comprising a first set of ribs and a second set of ribs protruding radially inward from an inner surface of the outer sleeve;
  a cam configured for axial translation with and disposed within the outer sleeve and comprising a first set of recessed and a second set of recesses such that the first and the second sets of recesses are alternately and circumferentially disposed around the cam between a plurality of protrusions extending radially outward from the cam;

an inner sleeve partially disposed within the outer sleeve, a first end of the inner sleeve being configured to engage with the cam to engage the first set of ribs with the first set of recesses that corresponds to a first operational stage or the second set of ribs with the second set of recesses that corresponds to a second operational stage; and a syringe comprising a first end portion coupled to a first end of the outer sleeve, and a second end portion disposed opposite the first end portion of the syringe.

2. The injector of claim 1, wherein:
the second end portion of the syringe is configured to extend through a second end of the inner sleeve in the first operational stage; and
the second end portion of the syringe is restricted from extending beyond the second end of the inner sleeve in the second operational stage.

3. The injector of claim 1, further comprising a biasing member positioned between the first end of the outer sleeve and the first end of the inner sleeve.

4. The injector of claim 1, wherein the syringe comprises a barrel, a needle mounted to an end of the barrel, a plunger, and a seal slidably mounted in the barrel, the plunger being disposed on the first end portion of the syringe and the needle being disposed on the second end portion of the syringe.

5. The injector of claim 4, wherein the inner sleeve comprises a plurality of ribs that extend radially inwards from an inner surface of the inner sleeve, and are configured to contact a portion of the barrel and restrict the needle from axially translating a distance beyond the second end of the inner sleeve.

6. The injector of claim 4, wherein a length of the first set of ribs corresponds to a stroke of the plunger within the barrel.

7. The injector of claim 4, wherein in the first operational state, the first set of recesses are configured to travel along a length of the first set of ribs as the plunger is depressed within the barrel, a distance that the plunger is depressed corresponds to the length of the first set of ribs.

8. The injector of claim 1, wherein:
a second end of the outer sleeve is disposed opposite the first end of the outer sleeve, and comprises a plurality of fingers, each having an interlocking groove disposed on an outer surface of a respective finger of the plurality of fingers; and
the plurality of fingers is configured to interlock with a cap, having an interlocking bead disposed on an inner surface of the cap, by engaging the interlocking grooves of the plurality of fingers with the interlocking bead of the cap.

9. The injector of claim 8, wherein the second end of the outer sleeve further comprises ramped projections that are sized to fit within recesses disposed on a receiving end of the cap, and comprise a surface inclined from a longitudinal axis of the outer sleeve.

10. The injector of claim 9, wherein when the ramped projections are positioned within the recesses of the cap and the cap is rotated in a circumferential direction of the injector, the inclined surfaces of the ramped projections are configured to contact the recesses of the cap and separate the cap from the outer sleeve by disengaging the interlocking grooves of the plurality of flexible members from the interlocking bead of the cap.

11. The injector of claim 1, wherein the syringe comprises a plunger that comprises a cap and at least one flexible arm extending from an interior surface of the cap, the at least one flexible arm is configured to be inserted into the first end of the outer sleeve and engage an aperture of the outer sleeve, thereby interlocking the syringe to the outer sleeve.

12. The injector of claim 11, wherein an exterior surface of the cap comprises an indicator that corresponds to a type of medicament contained within the syringe.

13. The injector of claim 1, wherein the inner sleeve comprises a window disposed within the inner sleeve, such that content of the syringe is visible from outside the inner sleeve.

14. The injector of claim 1, wherein:
the first end of the inner sleeve comprises a protrusion circumferentially disposed around the first end of the inner sleeve;
the second set of ribs comprises a shoulder disposed on a second end of the outer sleeve, the second end being opposite the first end of the outer sleeve; and
the protrusion is configured to contact the shoulder of the outer sleeve, such that the shoulder prevents a separation between the outer sleeve and the inner sleeve.

15. The injector of claim 1, wherein:
the syringe comprises a plunger coupled to the first end of the outer sleeve;
the cam comprising a plurality of angled protrusions circumferentially spaced around the cam; and
the first end of the inner sleeve comprises a plurality of angled protrusions circumferentially spaced around the inner sleeve and configured to engage the plurality of angled protrusions of the cam.

16. The injector of claim 15, wherein:
the first set of recesses of the cam are configured to travel along the first set of ribs as the plunger is depressed; and
in response to the first set of recesses traveling beyond the first set of ribs, the plurality of angled protrusions of the inner sleeve are configured to engage the plurality of angled protrusions of the cam and to impart a circumferential force on the cam causing the cam to rotate, thereby aligning the second set of ribs with the second set of recesses of the cam.

17. The injector of claim 16, wherein the rotation of the cam causes the plurality of angled protrusions of the cam and the inner sleeve to contact each other, thereby providing at least one of an audible or tactile feedback.

18. The injector of claim 1, wherein:
a second end of the inner sleeve comprises a ridge extending from an outer surface of the inner sleeve and is configured to engage with an adapter to secure the adapter to the injector; and
the adapter comprises a Luer adapter to deliver medicament intravenously or a nasal spray adapter to deliver medicament intranasally.

* * * * *

UNITED STATES PATENT AND TRADEMARK OFFICE
CERTIFICATE OF CORRECTION

PATENT NO. : 12,318,595 B2
APPLICATION NO. : 17/361912
DATED : June 3, 2025
INVENTOR(S) : Joseph B. Hoffer et al.

It is certified that error appears in the above-identified patent and that said Letters Patent is hereby corrected as shown below:

In the Specification

In the Description:

Column 5, Line 45, change "124-2" to -- 125-2 --

In the Claims

Claim 1, in Column 14, Line 66, change "recessed" to -- recesses --

Claim 7, in Column 15, Line 40, change "state" to -- stage --

Signed and Sealed this
Eighth Day of July, 2025

Coke Morgan Stewart
*Acting Director of the United States Patent and Trademark Office*